(12) United States Patent
Wegelin et al.

(10) Patent No.: US 11,373,509 B2
(45) Date of Patent: *Jun. 28, 2022

(54) PORTABLE COMPLIANCE DISPENSER

(71) Applicant: GOJO Industries, Inc., Akron, OH (US)

(72) Inventors: Jackson W. Wegelin, Stow, OH (US); Matthew J. Archer, Aurora, OH (US)

(73) Assignee: GOJO Industries, Inc., Akron, OH (US)

( * ) Notice: Subject to any disclaimer, the term of this patent is extended or adjusted under 35 U.S.C. 154(b) by 509 days.

This patent is subject to a terminal disclaimer.

(21) Appl. No.: 15/671,082

(22) Filed: Aug. 7, 2017

(65) Prior Publication Data

US 2017/0337803 A1 Nov. 23, 2017

Related U.S. Application Data

(60) Continuation of application No. 14/982,169, filed on Dec. 29, 2015, now Pat. No. 9,728,070, which is a division of application No. 13/095,052, filed on Apr. 27, 2011, now Pat. No. 9,262,905.

(51) Int. Cl.
| | |
|---|---|
| *G08B 23/00* | (2006.01) |
| *G08B 21/24* | (2006.01) |
| *A61L 2/00* | (2006.01) |
| *A61L 2/24* | (2006.01) |

(52) U.S. Cl.
CPC .......... *G08B 21/245* (2013.01); *A61L 2/0088* (2013.01); *A61L 2/24* (2013.01); *A61L 2202/14* (2013.01); *A61L 2202/16* (2013.01)

(58) Field of Classification Search
CPC ....... G08B 21/245; A61L 2/0088; A61L 2/24; A61L 2202/14; A61L 2202/16
See application file for complete search history.

(56) References Cited

U.S. PATENT DOCUMENTS

| | | | | |
|---|---|---|---|---|
| 5,199,118 | A * | 4/1993 | Cole | A47K 1/04 4/619 |
| 5,202,666 | A * | 4/1993 | Knippscheer | G08B 7/06 340/567 |
| 5,629,527 | A * | 5/1997 | Levitt | A61C 15/00 250/455.11 |
| 5,966,753 | A * | 10/1999 | Gauthier | A47K 5/12 4/628 |
| 6,125,482 | A * | 10/2000 | Foster | E03C 1/057 4/628 |
| 6,426,701 | B1* | 7/2002 | Levy | G08B 21/24 222/39 |

(Continued)

OTHER PUBLICATIONS

Akif Meydanci et al., RFID based hand hygiene compliance monitoring station (Year: 2013).*

(Continued)

*Primary Examiner* — Quang Pham
(74) *Attorney, Agent, or Firm* — Cooper Legal Group, LLC

(57) ABSTRACT

A portable compliance dispenser provides a compliance module that is removably attached to a replaceable refill container, which carries any suitable liquid material, such as sanitizer. The compliance module is configured to be worn or carried by an individual and communicates hygiene compliance data to a remote monitoring station when material from the refill container is dispensed.

20 Claims, 17 Drawing Sheets

(56) References Cited

U.S. PATENT DOCUMENTS

| | | | | |
|---|---|---|---|---|
| 6,780,383 B1* | 8/2004 | Ettlinger | A61L 2/26 | 43/132.1 |
| 6,882,278 B2* | 4/2005 | Winings | G16Z 99/00 | 340/573.4 |
| 7,375,640 B1* | 5/2008 | Plost | G08B 21/245 | 340/572.1 |
| 7,551,092 B1* | 6/2009 | Henry | G08B 21/245 | 340/286.07 |
| 7,597,122 B1* | 10/2009 | Smith | G08B 21/245 | 222/105 |
| 7,815,075 B2* | 10/2010 | Simkins | A47K 5/1201 | 222/509 |
| 8,038,034 B2* | 10/2011 | Pelfrey | B05B 11/3032 | 222/207 |
| 8,387,833 B2* | 3/2013 | LaFlamme | G01F 11/025 | 222/335 |
| 8,558,701 B2* | 10/2013 | Wegelin | G08B 21/245 | 340/573.1 |
| 8,988,228 B2* | 3/2015 | Iseri | B05B 11/00412 | 340/573.6 |
| 10,121,149 B2* | 11/2018 | Davis | G06Q 30/018 | |
| 2003/0019536 A1* | 1/2003 | Smith | G08B 21/245 | 141/18 |
| 2004/0001009 A1* | 1/2004 | Winings | G08B 21/245 | 340/870.16 |
| 2004/0090333 A1* | 5/2004 | Wildman | G16H 40/20 | 340/573.1 |
| 2005/0274195 A1* | 12/2005 | Mizuno | G01L 3/12 | 73/779 |
| 2006/0037229 A1* | 2/2006 | Lu | A01K 93/02 | 43/17 |
| 2006/0071799 A1* | 4/2006 | Verdiramo | G08B 21/245 | 340/573.5 |
| 2006/0272361 A1* | 12/2006 | Snodgrass | G08B 21/245 | 68/19 |
| 2006/0273915 A1* | 12/2006 | Snodgrass | G08B 21/245 | 222/52 |
| 2006/0289567 A1* | 12/2006 | Shoham | A61B 90/80 | 222/183 |
| 2007/0008719 A1* | 1/2007 | Hill | F21V 27/005 | 362/198 |
| 2007/0064986 A1* | 3/2007 | Johnson | G08B 21/245 | 382/128 |
| 2007/0183413 A1* | 8/2007 | Zusman | H01H 35/14 | 370/368 |
| 2007/0229288 A1* | 10/2007 | Ogrin | G08B 21/245 | 222/1 |
| 2008/0021779 A1* | 1/2008 | Lynn | G06Q 30/0268 | 705/14.65 |
| 2008/0087719 A1* | 4/2008 | Sahud | G08B 21/245 | 235/376 |
| 2008/0100441 A1* | 5/2008 | Prodanovich | G08B 21/245 | 340/572.1 |
| 2008/0210659 A1* | 9/2008 | McKinney | A45F 3/16 | 220/4.24 |
| 2008/0246599 A1* | 10/2008 | Hutton | G08B 21/245 | 340/529 |
| 2009/0195385 A1* | 8/2009 | Huang | G16H 40/20 | 340/572.1 |
| 2009/0224907 A1* | 9/2009 | Sinha | G08B 21/245 | 340/541 |
| 2009/0324444 A1* | 12/2009 | Stratmann | G08B 21/245 | 49/324 |
| 2010/0094581 A1* | 4/2010 | Cagle | G08B 21/245 | 702/176 |
| 2010/0117836 A1* | 5/2010 | Seyed Momen | G16H 40/20 | 340/573.1 |
| 2010/0134296 A1* | 6/2010 | Hwang | G08B 21/245 | 340/573.1 |
| 2010/0164728 A1* | 7/2010 | Plost | G08B 21/245 | 340/573.1 |
| 2010/0169111 A1* | 7/2010 | Brue | G16H 40/67 | 340/541 |
| 2010/0188228 A1* | 7/2010 | Hyland | G08B 31/00 | 340/572.1 |
| 2010/0206306 A1* | 8/2010 | Feriani | B05B 12/12 | 222/52 |
| 2010/0206976 A1* | 8/2010 | Salentine | A45F 5/004 | 242/379.2 |
| 2010/0207766 A1* | 8/2010 | Verdiramo | G08B 21/245 | 340/573.1 |
| 2010/0207767 A1* | 8/2010 | Verdiramo | G08B 21/245 | 340/573.1 |
| 2010/0238021 A1* | 9/2010 | Harris | A47K 5/06 | 235/375 |
| 2010/0315244 A1* | 12/2010 | Tokhtuev | G16H 40/20 | 340/603 |
| 2011/0054285 A1* | 3/2011 | Searle | A61M 5/16804 | 29/428 |
| 2011/0062182 A1* | 3/2011 | Reynolds | B05B 12/004 | 222/63 |
| 2011/0108578 A1* | 5/2011 | Wegelin | A47K 5/1217 | 222/372 |
| 2011/0154889 A1* | 6/2011 | Stafford | B29C 45/16 | 264/250 |
| 2011/0182652 A1* | 7/2011 | Chung | A61L 2/18 | 401/218 |
| 2011/0234598 A1* | 9/2011 | Scarola | G08B 21/245 | 345/440.1 |
| 2011/0254682 A1* | 10/2011 | Sigrist Christensen | G16H 40/20 | 340/539.12 |
| 2011/0277342 A1* | 11/2011 | Ishii | A47K 10/48 | 34/526 |
| 2011/0316701 A1* | 12/2011 | Alper | G08B 21/245 | 340/573.1 |
| 2012/0006848 A1* | 1/2012 | Reynolds | G01F 13/00 | 222/63 |
| 2012/0112914 A1* | 5/2012 | Wegelin | G07C 3/00 | 340/573.1 |
| 2012/0218106 A1* | 8/2012 | Zaima | G16H 40/63 | 340/540 |
| 2012/0245729 A1* | 9/2012 | Wegelin | G01F 15/068 | 700/231 |
| 2012/0248140 A1* | 10/2012 | Iseri | A61L 2/18 | 222/1 |
| 2012/0268277 A1* | 10/2012 | Best | G08B 21/245 | 340/573.1 |
| 2013/0025714 A1* | 1/2013 | Hermann | G08B 21/245 | 137/551 |
| 2013/0334248 A1* | 12/2013 | Iseri | G08B 21/245 | 222/207 |
| 2014/0253334 A1* | 9/2014 | Hanlin | G08B 21/245 | 340/573.1 |
| 2014/0266575 A1* | 9/2014 | Pelfrey | A47K 5/1217 | 222/23 |
| 2014/0347185 A1* | 11/2014 | Smith | A61L 2/0088 | 222/52 |

OTHER PUBLICATIONS

Bal et al., A system for monitoring hand hygiene compliance based-on Internet-of-Things (Year: 2017).*

Anno et al., Arduino-based Automated Washroom Sanitizing System (Year: 2020).*

Jinadatha et al., Interaction of healthcare worker hands and portable medical equipment a sequence analysis to show potential transmission opportunities (Year: 2017).*

Loong et al., A Smart Location-Aware Hand Sanitizer Dispenser System (Year: 2020).*

Anto et al., Arduino-based Automated Washroom Sanitizing System (Year: 2020).*

Debes et al., Monitoring Activities of Daily Living in Smart Homes Understanding human behavior (Year: 2016).*

Patil et al., IoT Based Energy Efficacious Smart Hygiene System (Year: 2021).*

(56) References Cited

OTHER PUBLICATIONS

Wan et al., Human-subject tracking and localization fora hand hygiene monitoring system (Year: 2014).*

* cited by examiner

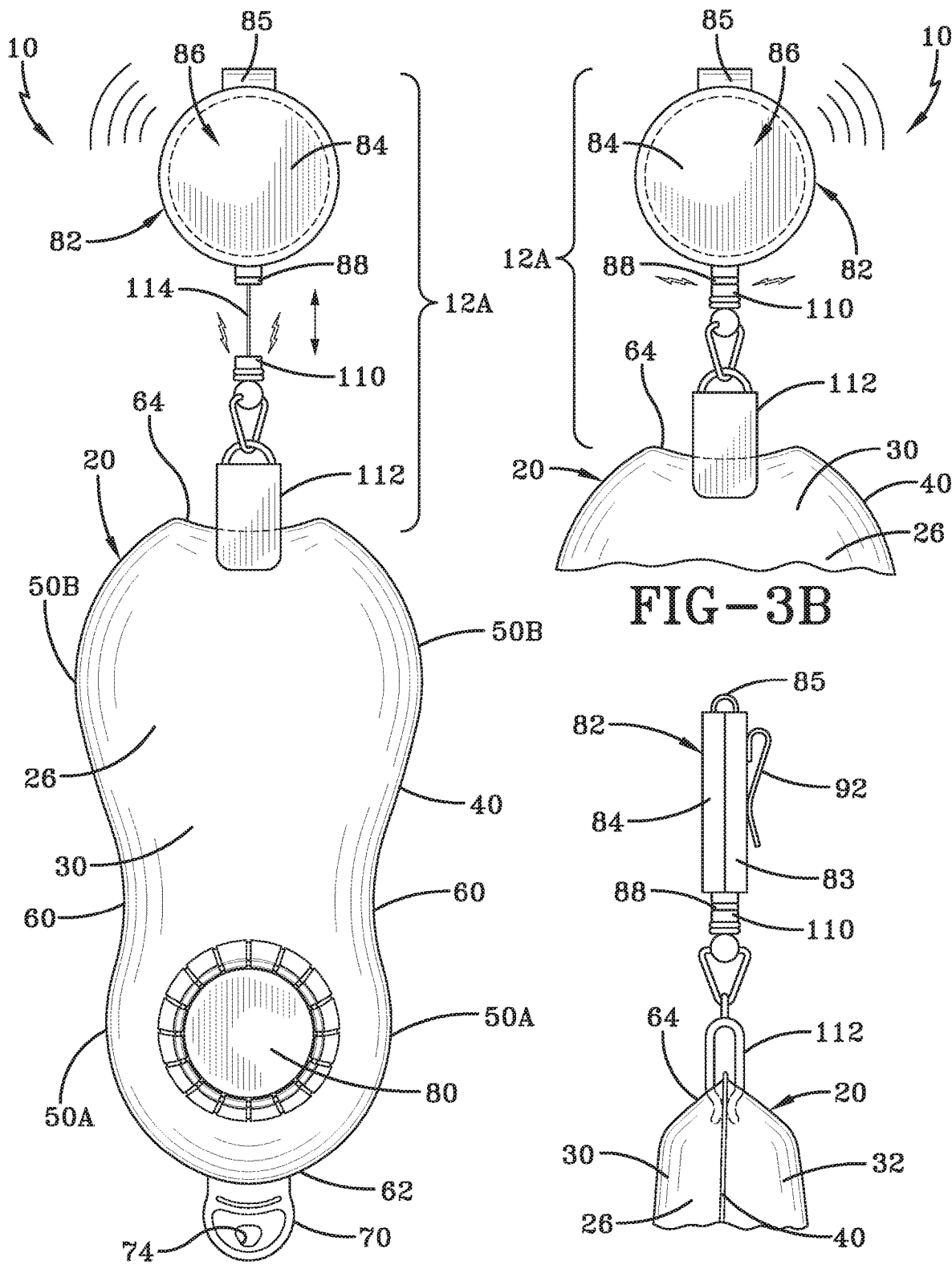

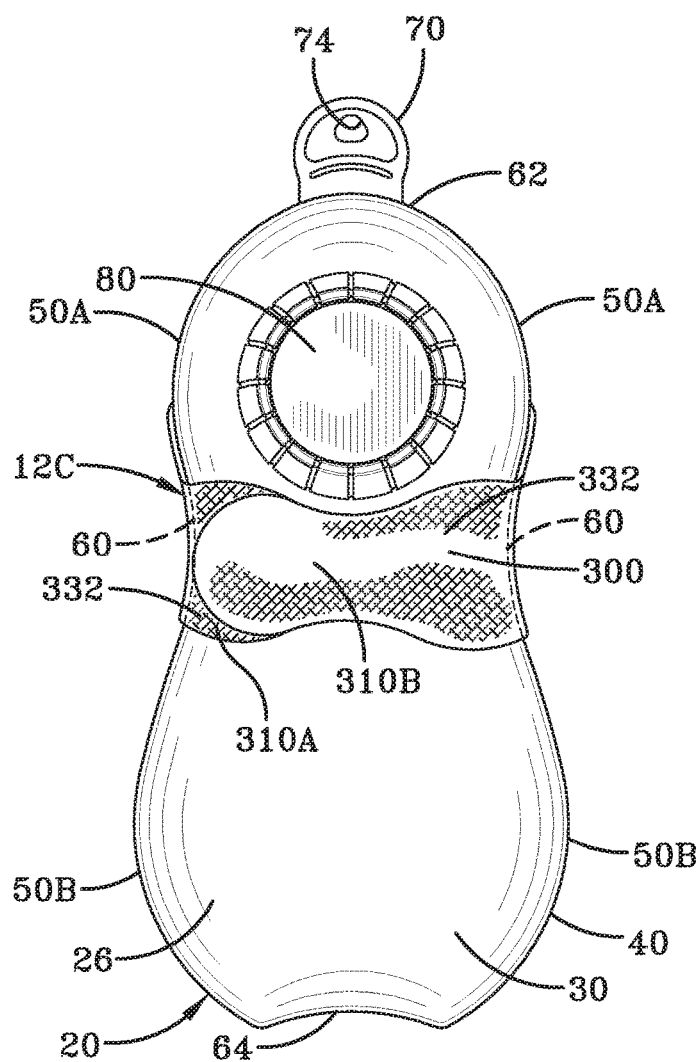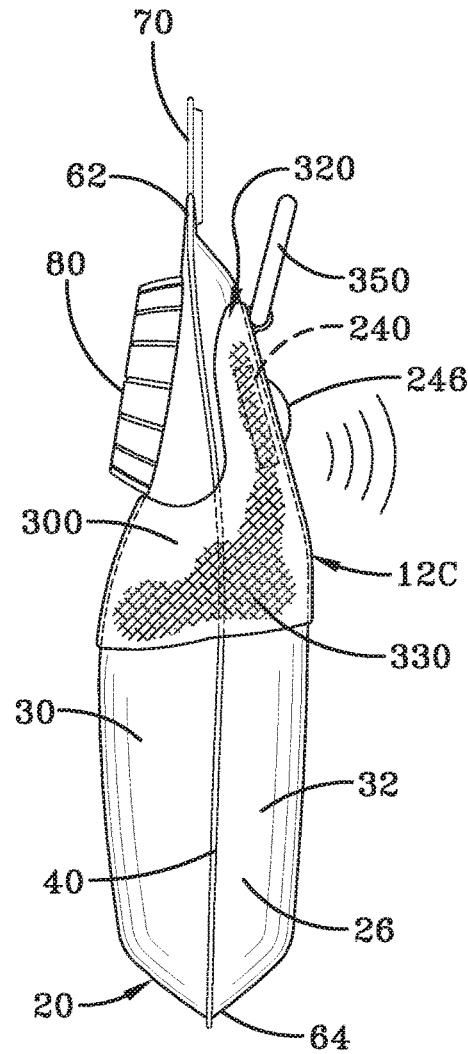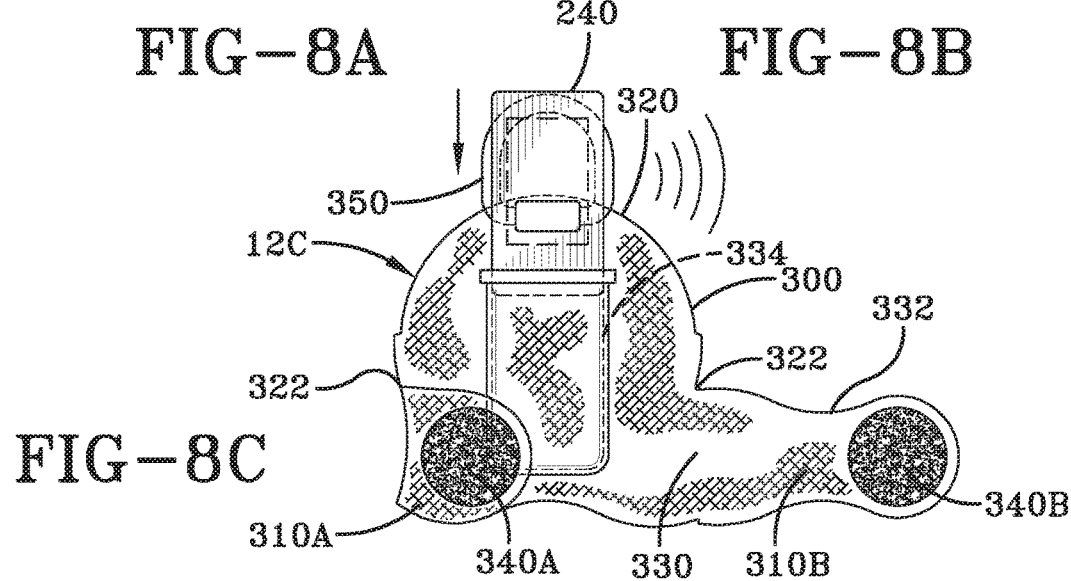

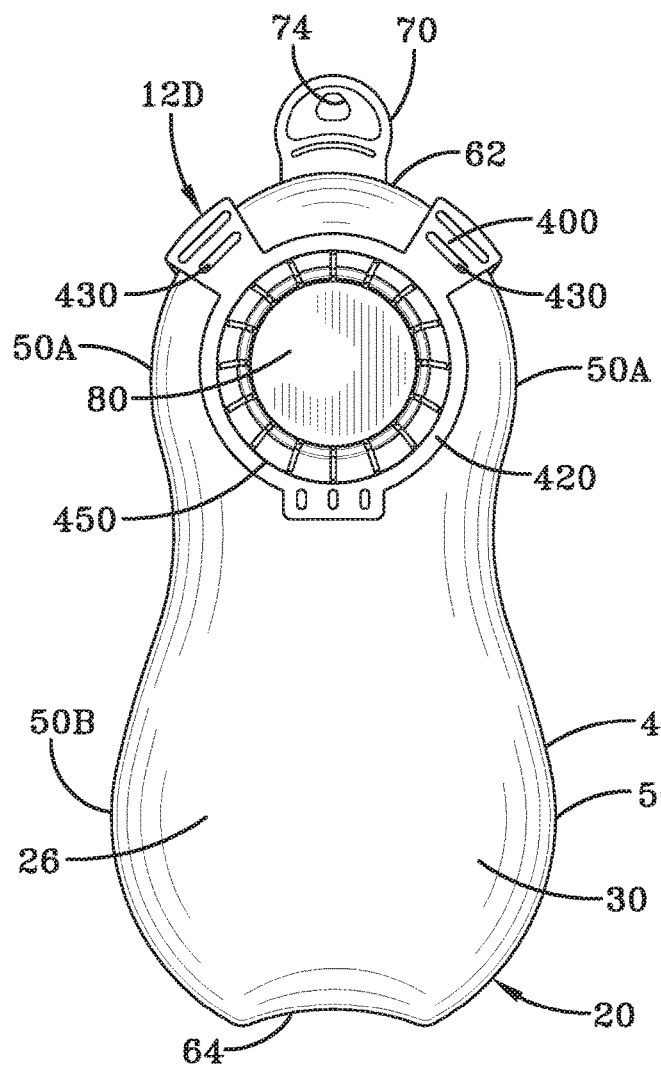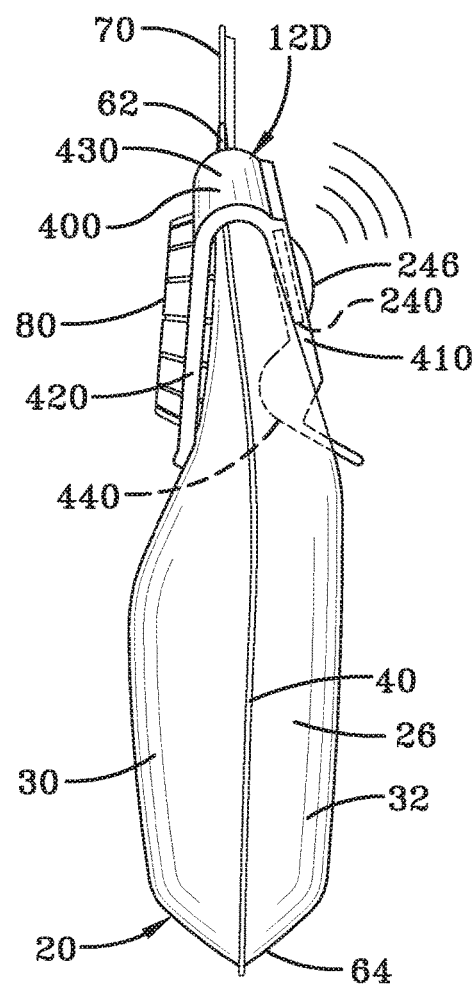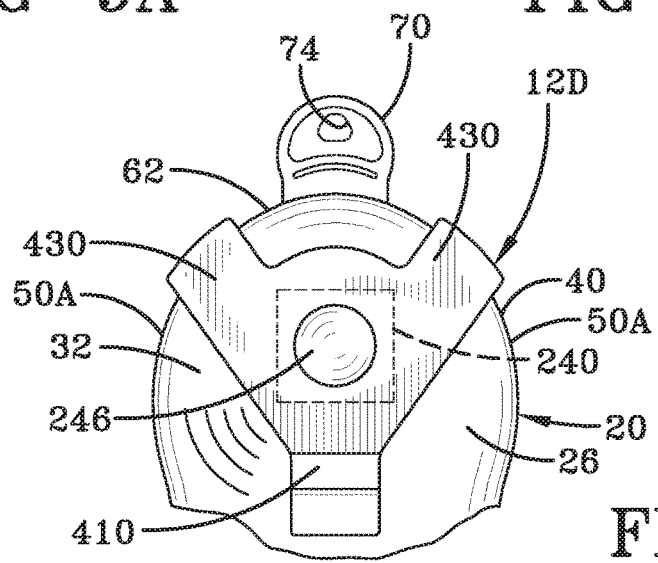
FIG-9A
FIG-9B
FIG-9C

PORTABLE COMPLIANCE DISPENSER

RELATED APPLICATIONS

This application is a continuation of and claims priority to U.S. patent application Ser. No. 14/982,169, titled "PORTABLE COMPLIANCE DISPENSER" and filed on Dec. 29, 2015, which was a divisional of U.S. patent application Ser. No. 13/095,052, titled "PORTABLE COMPLIANCE DISPENSER" and filed on Apr. 27, 2011. The contents of these applications are incorporated herein by reference.

TECHNICAL FIELD

The present invention generally relates to dispensers, such as sanitizer dispensers. In particular, the present invention relates to portable dispensers capable of collecting hygiene compliance data. More particularly, the present invention relates to portable dispensers that collect and transmit hygiene compliance data to a remote monitoring station.

BACKGROUND OF THE INVENTION

Recently, the public has become increasingly concerned with disease and its transmission, and as such, there is an increased awareness of the importance of hand cleansing and hygiene in general. For example, with respect to the transmission of *E. coli* in the food services industry, the rhinovirus in elementary schools, and nosocomial diseases within healthcare facilities, numerous studies have cited hand hygiene as an effective measure to guard against disease transmission. In response, health care, food service, and hotel and travel industries have been forced to examine their hygiene protocols and procedures to ensure that their personnel are adopting habits that are efficacious in the prevention of disease transmission.

In order to minimize the possibility of the transmission of bacteria or viruses by hand washing, full compliance with hand washing hygiene standards must be observed, as the failure of one individual to properly sanitize his or her hands can negate the efforts of others who come in contact with such individual. Thus, to ensure employees or other individuals have sufficient access to sanitizer, the current trend has been to permanently install full-size dispensers at designated areas throughout a building or work area. Such dispensers are rigidly affixed to a wall or counter and are capable of being refilled with sanitizer when they are emptied.

Unfortunately, such full-size fixed dispensers require that users return to them each time they are in need of sanitizer, which is inconvenient as users generally require multiple sanitizer applications throughout the day. Also, if the user is required to travel out of his or her way to obtain the sanitizer from the fixed dispenser, then he or she may be less inclined to sanitize their hands in accordance with predetermined hygiene protocols. In addition, installation of a sufficient quantity of fixed sanitizer dispensers to provide complete coverage throughout a facility, such as a hospital, would require a substantial cost. Moreover, in such a circumstance where there is a substantial number of full-size, fixed dispensers installed, an employee must periodically refill the sanitizer dispensers, which is costly and time consuming.

Alternatively, while portable dispensers are available, they are inconvenient to refill with liquid material, such as soap or sanitizer. In addition, such portable dispenser devices fail to acquire hygiene compliance data, which is desirable.

Therefore, there is a need for a portable compliance dispenser that is worn or carried by a user. In addition, there is a need for a portable compliance dispenser that is able to dispense liquid material, such as sanitizer, that collects and transmits hygiene compliance data to a remote monitoring station. Still yet, there is a need for a portable compliance monitor that dispenses liquid material, such as sanitizer, from a replaceable refill container.

SUMMARY OF THE INVENTION

In light of the foregoing, a portable dispenser comprises a refill container defining an interior within which a material is contained and from which the material is dispensed. A compliance module is attached to the refill container. The compliance module comprises an attachment clip attached to the refill container. A tether is attached to the attachment clip. A carrying case is attached to the tether. The carrying case urges the tether into a retracted position in which the carrying case is adjacent to the refill container.

According to another example, a portable dispenser comprises a refill container defining an interior within which a material is contained and from which the material is dispensed. The portable dispenser comprises a compliance module attached to the refill container. The compliance module comprises an attachment clip attached to the refill container, a switch, and a tether. The tether has a first end, which is attached to the attachment clip, and a second end, which is attached to the switch. The tether is movable between a retracted position, in which the switch is in a first state, and an extended position, in which the switch is in a second state.

According to another example, a portable dispenser comprises a refill container defining an interior within which a material is contained and from which the material is dispensed. A compliance module is attached to the refill container. The compliance module comprises an attachment clip attached to the refill container, a magnet attached to the attachment clip, a magnetic switch, and a tether. The tether has a first end, which is attached to the magnet, and a second end, which is attached to the magnetic switch. The tether is movable between a retracted position, in which the magnetic switch is in a first state and detects the presence of the magnet, and an extended position, in which the magnetic switch is in a second state and does not detect the presence of the magnet.

BRIEF DESCRIPTION OF THE DRAWINGS

These and other features and advantages of the present invention will become better understood with regard to the following description, appended claims, and accompanying drawings where:

FIG. 3A is an elevational view of one embodiment of a portable compliance dispenser showing the refill container separated from a compliance module in accordance with the concepts of the present invention;

FIG. 3B is a partial elevational view of the portable compliance module of FIG. 3A showing the refill container magnetically coupled to the compliance module in accordance with the concepts of the present invention;

FIG. 3C is a side elevational view of the portable compliance module of FIG. 3A in accordance with the concepts of the present invention;

FIG. 8A is an elevational view of an alternate portable compliance dispenser retained to the refill container by a fabric body in accordance with the concepts of the present invention;

FIG. 8B is a side elevational view of the portable compliance dispenser of FIG. 8A in accordance with the concepts of the present invention;

FIG. 8C is an elevational view of the portable compliance dispenser of FIG. 8A showing the retention arms used to attach the compliance module to the refill container in accordance with the concepts of the present invention;

FIG. 9A is an elevational view of another embodiment of the portable compliance dispenser having a compliance module that comprises a clip that is retained to the refill container in accordance with the concepts of the present invention;

FIG. 9B is a side elevational view of the portable compliance dispenser of FIG. 9A in accordance with the concepts of the present invention;

FIG. 9C is an elevational view of the clip used to retain the compliance module of FIG. 9A to the refill container in accordance with the concepts of the present invention;

DETAILED DESCRIPTION

Figure 1:
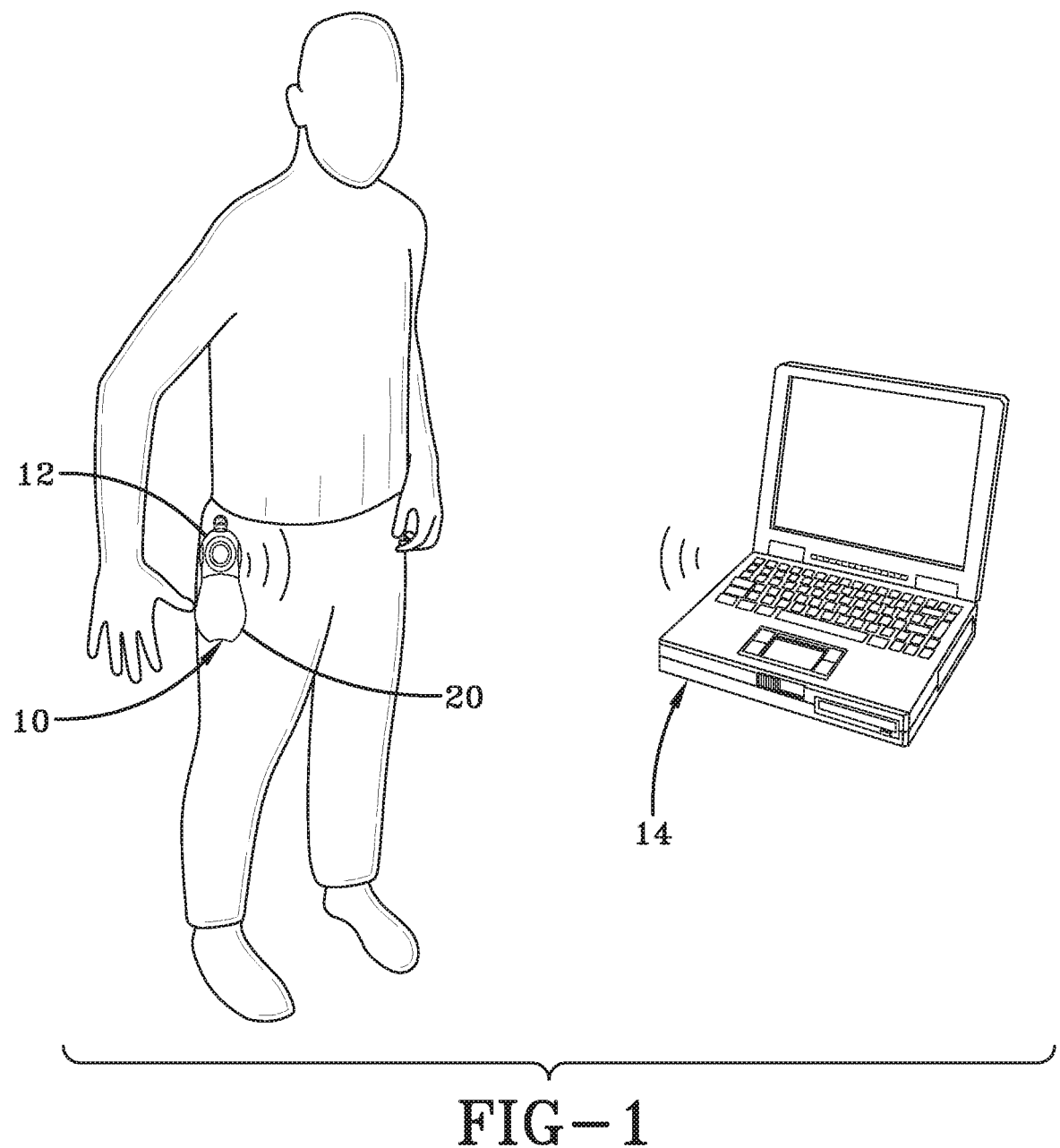
FIG. 1 is a perspective view showing a portable compliance dispenser in communication with a remote monitoring station in accordance with the concepts of the present invention.

A product dispensing system, depicted in FIG. 1, dispenses a measured amount of fluid product according to the embodiments of the subject invention. In one exemplary instance, the dispensing system, shown generally at 10, dispenses hand care products like soap, lotion or sanitizers, although other types of products may similarly be dispensed from the dispensing system.

A portable compliance dispenser that is wearable by an individual is generally referred to by the numeral 10, as shown in FIG. 1 of the drawings. The dispenser 10 comprises a compliance module 12 that wirelessly communicates hygiene compliance data with a remote monitoring station or compliance monitor 14 when liquid material, such as sanitizer, is dispensed from a refill container 20 that is operatively coupled to the module 12. Thus, the portable compliance dispenser 10 provides a manner in which liquid material, such as sanitizer, can be portably dispensed from a replaceable refill container while collecting and communicating hygiene compliance data associated with its usage.

Figures 2A, 2B:
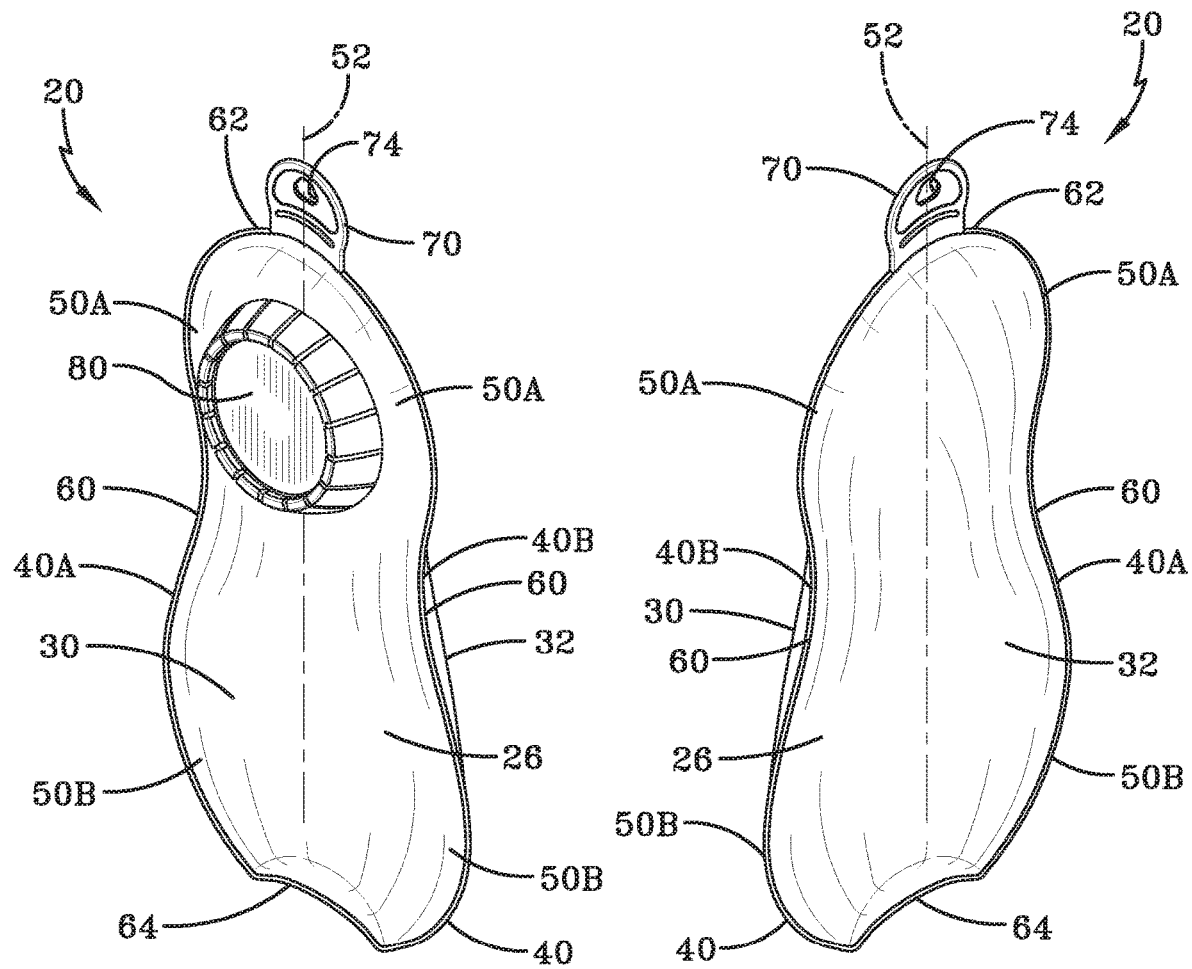
FIG. 2A is a perspective view of a front section of a refill container used by the portable compliance dispenser that contains liquid material to be dispensed in accordance with the concepts of the present invention.
FIG. 2B is a perspective view of a rear section of the refill container in accordance with the concepts of the present invention.
Figure 2C:
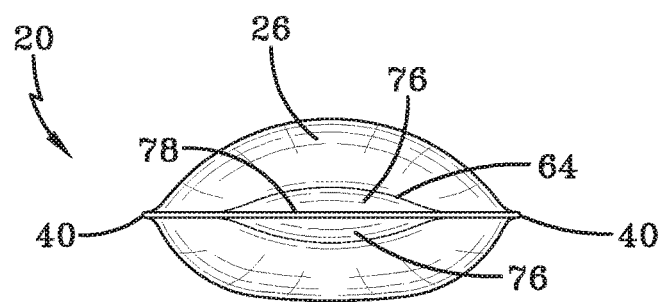
FIG. 2C is a bottom plan view of the attachment end of the refill container in accordance with the concepts of the present invention.
Figure 4:
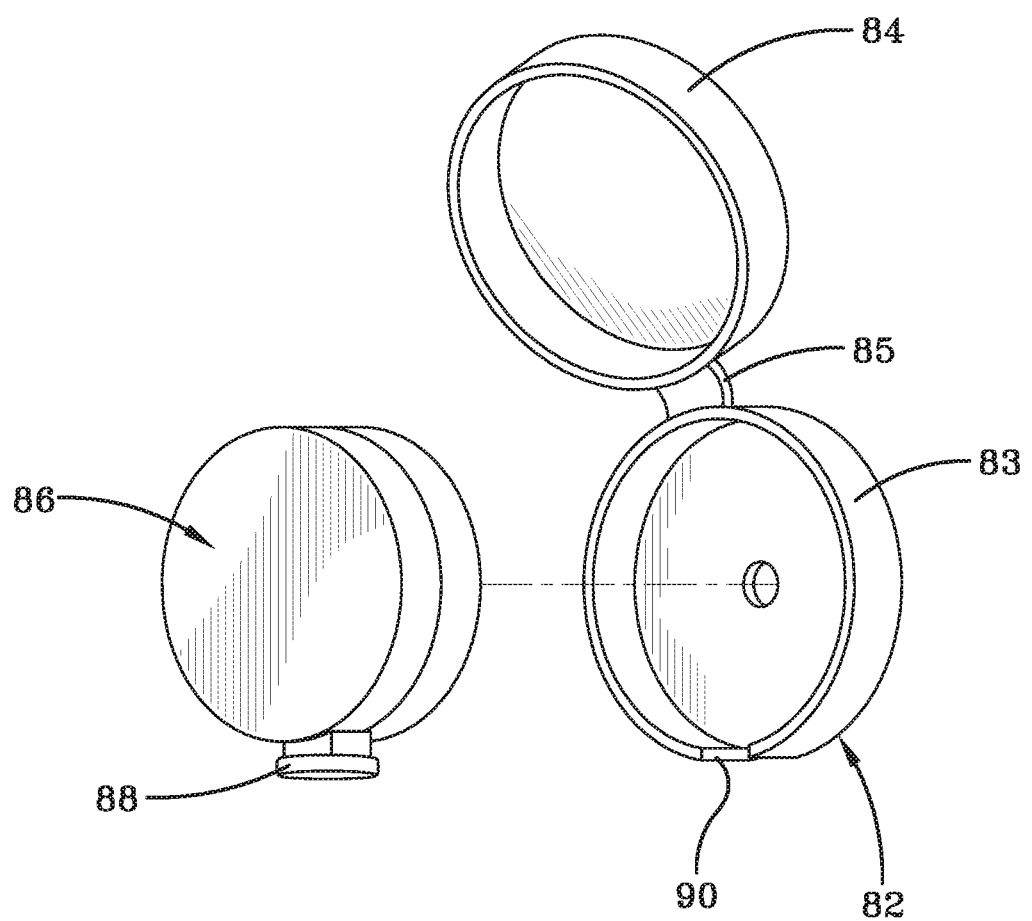
FIG. 4 is a perspective view of a communication module removably retained in a carrying case provided by the compliance module shown in FIG. 3A in accordance with the concepts of the present invention.

Specifically, the portable compliance dispenser 10 comprises a plurality of compliance modules 12, which are designated by identifiers A-G. Specifically, the compliance modules 12A-F are configured for attachment with the refill container 20 shown in FIGS. 2A-C, while compliance module 12G is configured for attachment to a dispensing container to be discussed below. The refill container 20 is configured as a modular unit and is able to carry an amount of any liquid material, such as soap, sanitizer, or moisturizer for example. Specifically, the refill container 20 comprises an elongated body 26 formed of any suitable material, such as plastic, and has opposed front and rear sections 30 and 32, which are joined about an edge 40 having opposed lateral portions 40A and 40B. The lateral portions 40A-B of the edge 40 are defined by two pairs of substantially rounded or curved shoulder sections 50A and 50B, which extend away from a central midline 52 of the refill container 20. The pairs of shoulders 50A and 50B are spaced apart along the midline 52 to form a waist 60 in the region therebetween that is approximately in the middle of the refill container 20. The refill container 20 includes a dispensing end 62 that is proximate to the shoulders 50A, and an opposed attachment end 64 that is proximate to the shoulders 50B. Extending from the edge 40 of the refill container 20 at the dispensing end 62 is a tab 70 that includes a dispensing port 74 that is in fluid connection with the liquid material contained in the refill container 20. The attachment end 64 of the refill container 20 includes a cavity 76, as shown in FIG. 2C, with a substantially planar attachment section 78 extending from the edge 40. The front section 30 of the refill container 20 also includes a pump element, such as dome pump 80 that when compressed by a user's hand or fingers, generates the necessary pressure to force the liquid material out of the dispensing port 74, thereby dispensing the liquid material to the user. As such, the shape and configuration of the refill container 20 is modular, allowing it to be compatible with the various compliance modules 12A-F that are discussed in detail below. In one aspect, the refill container 20 may comprise a pouch, for example.

In one embodiment of the portable compliance dispenser 10, a compliance module 12A is shown in FIGS. 3A-C and 4. Specifically, the compliance module 12A comprises a carrying case 82, shown clearly in FIG. 4, which includes a base 83 that is pivotably attached to a lid 84 by a hinge 85, such as a living hinge. The base 83 is configured to house and retain a communication module 86, which includes a magnetic switch 88 that is dimensioned to be received within a notch 90 disposed in the periphery of the base 83. As such, when the module 86 is disposed within the base 83, the lid 84 may be closed and retained to the base 83 using any suitable means, such as a snap, latch, or the like. The case 82 also includes a carrying clip 92 that is suitable for removably attaching the case 82 to the user. The magnetic switch 88 is configured to detect the proximity of the container magnet 110 that is carried by or otherwise attached to an attachment clip 112 that is attached (or removably attached) to the refill container 20. It should be appreciated that the attachment clip 112 may be coupled to the refill container 20 using any suitable means of fixation, including compressive attachment or adhesive for example. Furthermore, the magnetic switch 88 and the container magnet 110 are joined by a retractable tether 114, which may comprise any suitable cable, cord, line, or the like, or alternatively, the tether 114 may comprise an elastic cord or band that is configured to elastically urge the container magnet 110 and the magnetic switch 88 together. In other words when the compliance module 12A is in use, the tether 114 serves to normally urge the container magnet 110, as well as the refill container 20, to be proximate to the communication module 86 such that the magnetic switch 88 detects the presence of the container magnet 110. Alternatively, when the refill container 20 is to be used, the tether 114 allows the refill container 20 and container magnet 110 to be pulled or moved away from or outside of the magnetic detection range of the magnetic switch 88.

Figure 5:
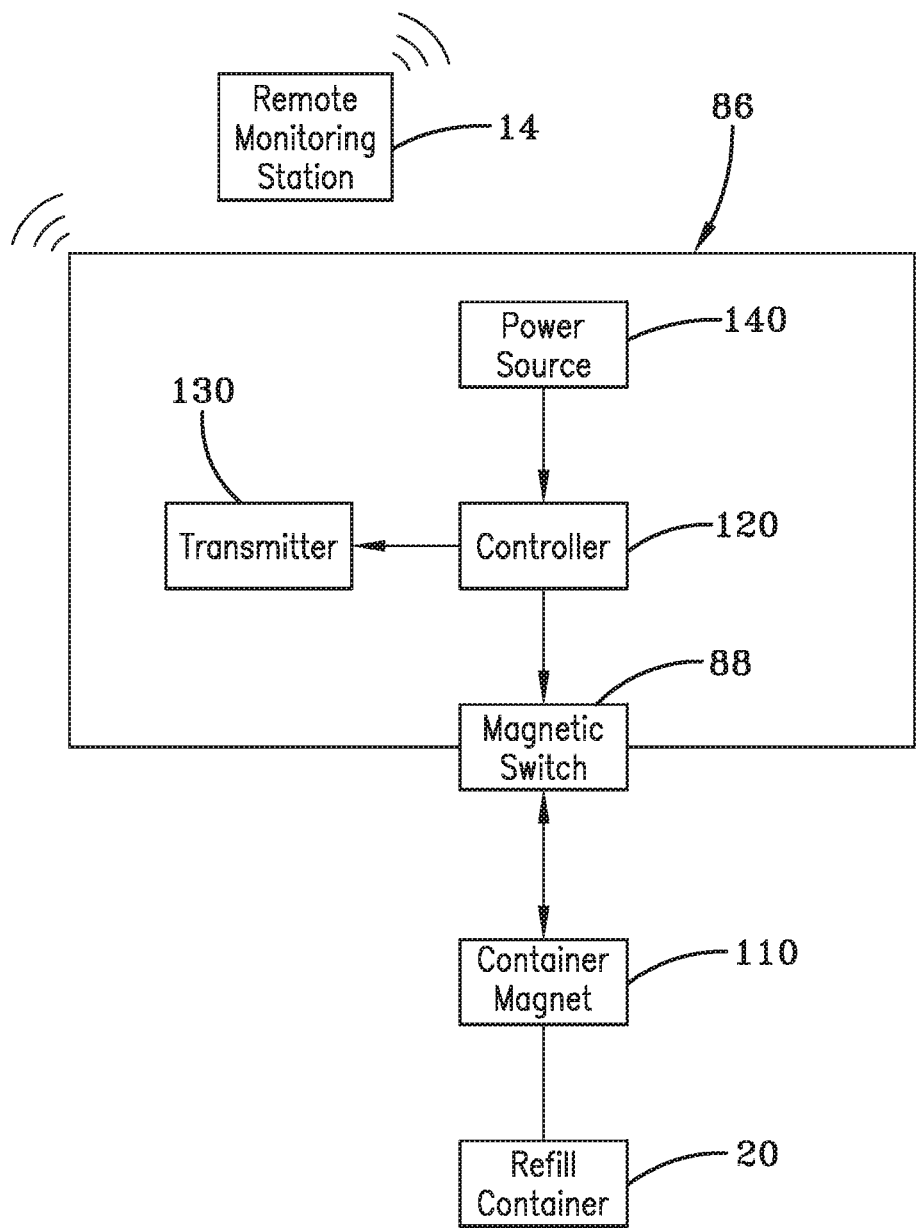
FIG. 5 is a block diagram of the communication module utilized by the portable compliance dispenser shown in FIGS. 3A-C in accordance with the concepts of the present invention.

The communication module 86, shown in FIG. 5, comprises a controller 120 that includes the necessary hardware and/or software to carryout the functions to be discussed. Coupled to the controller 120 is a wireless transmitter 130 that is configured to transmit or otherwise communicate wireless signals, such as a hygiene compliance signal, that contain hygiene compliance data to the remote monitoring station 14 in a manner to be discussed. In one aspect, the transmitter 130 may be replaced with a transceiver that is capable of transmitting and receiving data to and from the remote monitoring station 14. The magnetic switch 88 is coupled to the controller 120, which is configured to detect the presence and non-presence of the container magnet 110, as previously discussed. Moreover, the controller 120 and the transmitter 130 are powered by a power source 140, such as a battery or solar cell for example.

The remote monitoring station 14 that is used to communicate with the compliance module 12A, as well as compliance modules 12B-G to be discussed, comprises any suitable computing system that is configured to receive the wireless hygiene compliance signal and data sent from the compliance modules 12A-G. In one aspect, the remote monitoring station 14 may include input and output devices, such as a keyboard, mouse, and monitor. This allows users of the monitoring station 14 to analyze and process the received hygiene compliance data to determine if individuals wearing the compliance modules 12A-G are in compliance with predetermined hygiene standards and protocols.

Thus, during operation of compliance module 12A, the tether 114 is in a normally retracted state such that the container magnet 110 is within the detection range of the container magnet 110. As such, when the container magnet 110 is moved out of the detection range of the magnetic switch 88 by extending the tether 114 in order to dispense material from the refill container 20, the compliance module 12A transmits a wireless hygiene compliance signal or compliance data to the remote monitoring station 14 via the transmitter 130 to indicate that the refill container 20 is being used and that a hygiene compliance and dispensing event has occurred. That is, the remote monitoring station 14 identifies the transmission of the hygiene compliance signal or compliance data and records it as a completion of a hygiene compliance event, signifying that liquid material in the refill container 20 has been dispensed from the dispensing port 74 by the user of the dispenser 10 by depression of the dome pump 80. After the dispensing event has been completed and the tether 114 is retracted such that the presence of the container magnet 110 is detected by the magnetic switch 88, the transmitter 130 is disabled so that it does not transmit the compliance signal or data.

It should be appreciated that each compliance module 12A may be assigned a unique identification code that is associated with transmitted hygiene compliance signal and data sent to the remote monitoring station 14. This allows an administrator of the monitoring station 14 to identify and discretely monitor one or more users wearing the compliance module 12A to determine if he or she is in compliance with predetermined hygiene standards and protocols, based on the collected hygiene compliance data.

Figure 6A:
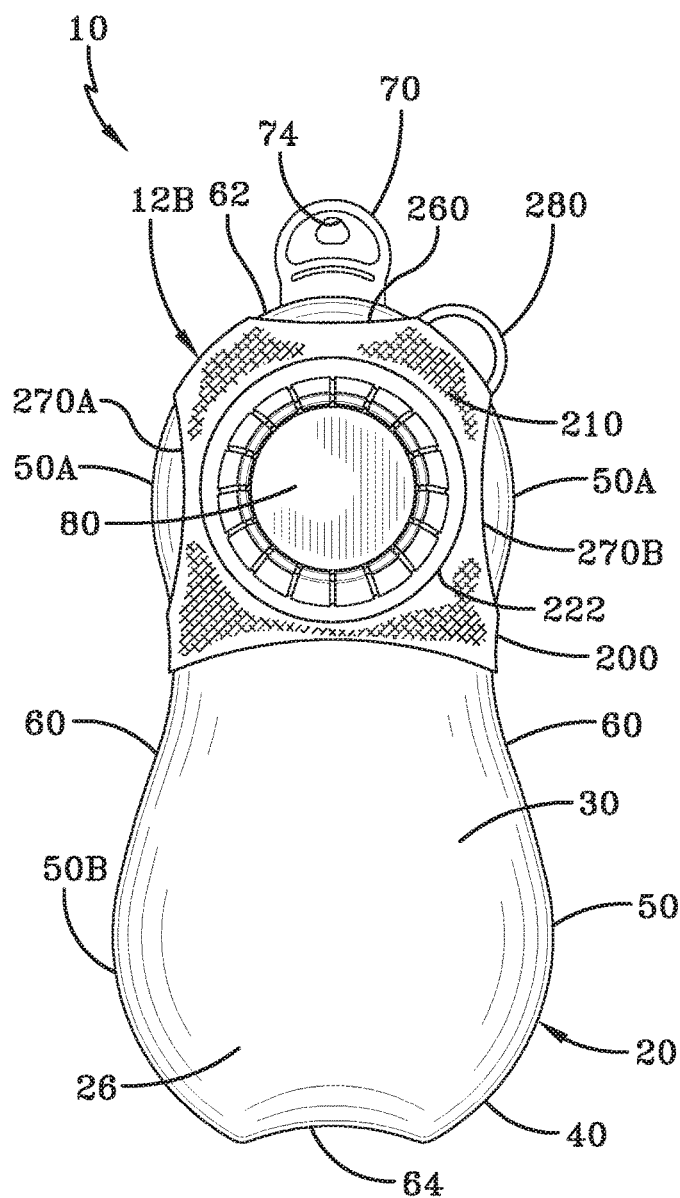
FIG. 6A is a front elevational view of an alternate portable compliance dispenser in which a compliance module comprises a stretchable sleeve that is attached to the refill container in accordance with the concepts of the present invention.
Figure 6B:
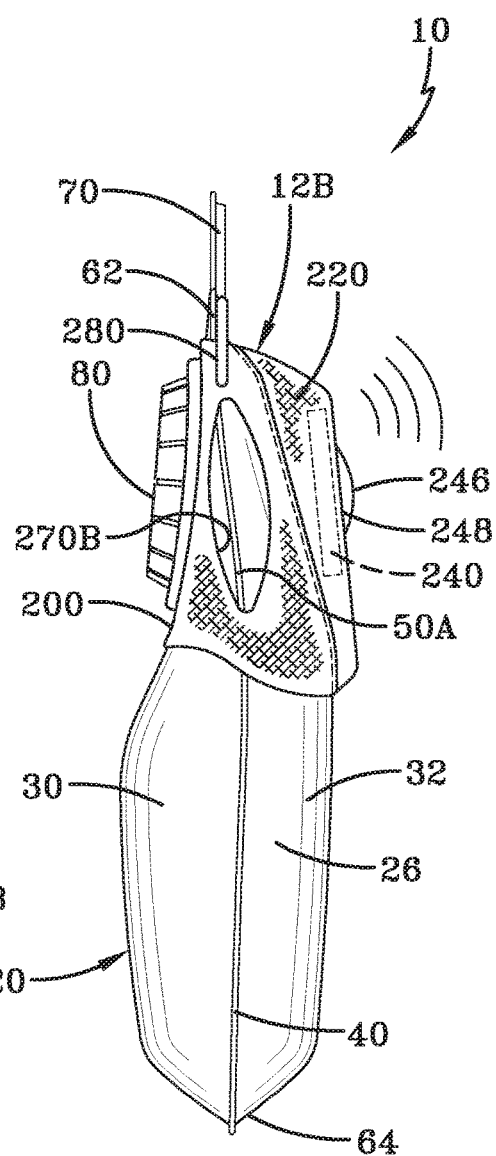
FIG. 6B is a side elevational view of the portable compliance dispenser of FIG. 6A in accordance with the concepts of the present invention.

In another embodiment of the portable compliance dispenser 10, a compliance module 12B for use with the refill container 20 is shown in FIGS. 6A-B. The compliance module 12B comprises a sleeve 200, which may be formed from any suitable material, such as fabric, as well as stretchable material including latex, neoprene, or the like. The sleeve 200 includes opposed front and rear sections 210 and 220 that form a cavity to receive the refill container 20 therein. As such, when the sleeve 200 is installed, the front section 210 of the sleeve 200 is configured to be disposed adjacent to the front section 20 of the refill container 20, such that the dome pump 80 of the refill container 20 is received through a receiving aperture 222 provided by the front section 210 of sleeve 200.

Figure 7:
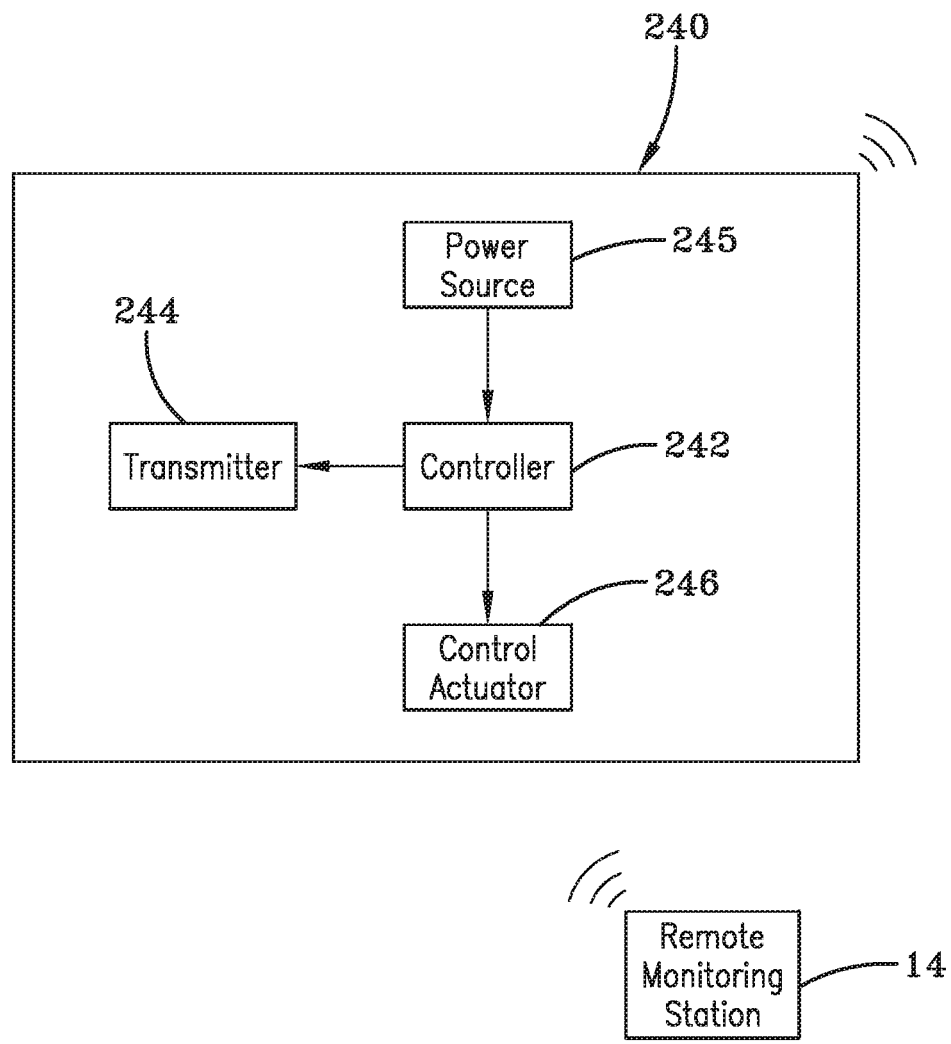
FIG. 7 is a block diagram of another communication module utilized by alternative portable compliance modules in accordance with the concepts of the present invention.

A communication module 240 is embedded within the rear section 220 of the sleeve 200, such that it is adjacent to the rear section 32 of the refill container 20 when the sleeve 200 is installed over the refill container 20. The communication module 240, shown in detail in FIG. 7, includes a controller 242, which has the necessary hardware and/or software that is needed to carryout the functions to be discussed. Coupled to the controller 242 is a wireless transmitter 244 that is configured to transmit a hygiene compliance signal and data to the remote monitoring station 14. In one aspect, the transmitter 244 may comprise a transceiver that is capable of transmitting and receiving data to and from the remote monitoring station 14. The communication module 240 is powered by a power source 245, such as a battery or solar cell for example. A control actuator 246 is coupled to the controller 242 and is configured to extend through an actuator aperture 248 disposed through the rear section 220 of the sleeve 200. However, it is also contemplated that the control actuator 246 may be maintained beneath the rear section 220 of the sleeve 200 as well, so that it is hidden from view. It should be appreciated that the control actuator 246 may comprise a manually-actuated button or switch or may comprise any touch or pressure-sensitive sensor. In one aspect, the control actuator 246 may comprise a biometric sensor that is configured to detect a fingerprint, for example. The communication module 240 is configured to transmit a wireless hygiene compliance signal and data when the control actuator 246 is actuated. Moreover, the communication module 240 is assigned a unique identification code that is associated with the transmitted hygiene compliance signal and data. This allows an administrator of the compliance station 14 to identify and discretely monitor one or more users wearing the compliance module 12B to determine if he or she is in compliance with predetermined hygiene standards and protocols, based on the collected hygiene compliance data.

Disposed about the periphery of the sleeve 200 is a top aperture 260 and two laterally-oriented and opposed shoulder apertures 270A and 270B, which are dimensioned to respectively receive the tab 70 and the shoulders 50A that extend from the refill container 20. As such, when the refill container 20 is received or at least partially received within the sleeve 200, the tab 70 is permitted to extend through the top aperture 260, while the shoulders 50A are dimensioned so that they extend through the shoulder apertures 270A and 270B. As a result, the control actuator 246 is disposed through the actuator aperture 248 in the rear section 220 of the sleeve 200 and is substantially aligned with the dome pump 80 disposed through the receiving aperture 222 in the front section 210 of the sleeve 200.

In order to attach the compliance module 12B to a user or individual, an attachment loop 280 is provided, which extends from the sleeve 200 at a point between the top aperture 260 and the shoulder aperture 270B, although the attachment loop 280 may be provided at any desired position on the sleeve 200.

Thus, during operation of the communication module 12B, the user squeezes or otherwise depresses the dome pump 80, while engaging the control actuator 246 with his or her fingers. The compression of the dome pump 80 dispenses the liquid material from the refill container 20, while the engagement of the control actuator 246 causes the wireless hygiene compliance signal and associated hygiene compliance data to be transmitted from the transmitter 244 to the remote compliance monitoring station 14. The monitoring station 14 records the received compliance signal as a completed hygiene event that is associated with the specific identification code assigned to the specific compliance module 12B. It should be appreciated that the manner of operation of compliance module 12B and the communication module 240 used therewith is equivalent to that of compliance modules 12C-F, which are discussed in detail below.

In yet another embodiment of the portable compliance dispenser 10, a compliance module 12C for use with the refill container 20 is shown in FIGS. 8A-C. Specifically, the control module 12C comprises a body 300 having opposed retention arms 310A and 310B extending therefrom at a substantially right angle, which may comprise any suitable material, such as fabric, including stretchable material, such as neoprene, latex, or the like. In one aspect, the body 300 may have a substantially curved upper edge 320 that terminates at points 322 where each retention arm 310A-B extends from the body 300 at a substantially right angle. The body 300 has opposed inner and outer surfaces 330,332, with a compartment 334 disposed on the outer surface 332. Removably received within the compartment 334 is the communication module 240, as previously discussed, which includes the control actuator 246. It should also be appreciated that the communication module 240 may be carried in a housing, such as an impact-resistant housing, so that it can be readily removed and reinstalled into another compliance module 12C as desired.

The retention arms 310A-B include respective attachment sections 340A and 340B, such that the attachment section 340A is provided on the outer surface 332 of the retention arm 310A, and the attachment section 340B is provided on the inner surface 340 of the retention arm 301B. It should be appreciated that the attachment sections 340A-B may comprise hook and loop material, such as VELCRO®, or any other suitable material or device, such as a snap button, clip, tie, or the like. As such, the arms 310A-B of the body 300 are wrapped around the waist 60 of the body 26 of the refill container 20 and retained thereabout by coupling the attachment sections 340A-B together, such that the control actuator 246 is substantially aligned with the dome pump 80.

To facilitate the attachment of the compliance module 12C to a user, an attachment ring 350 is coupled to the rear surface 332 of the body 300, allowing the compliance module 12C to be removably attached to a belt loop or other item on the user.

Thus during operation of the compliance module 12C, the control actuator 246 is engaged, and the dome pump 80 is depressed, resulting in the liquid material being dispensed from the refill container 20 and the hygiene compliance signal, compliance data, and identification code being transmitted from the remote communication module 240 to the remote monitoring station 14, as discussed with regard to compliance module 12B.

In another embodiment of the portable compliance dispenser 10, a portable compliance module 12D for use with the refill container 20 is shown in FIGS. 9A-C. The portable compliance module 12D includes a body 400 that comprises a retention arm 410 that is coupled to a retention ring 420 by a pair of coupling arches 430. In one aspect, the body 400 may be formed from any suitable material, such as plastic, steel, or aluminum, for example. The compliance module 12D is attached to the refill container 20, so that the retention arm 410 is adjacent to the rear section 32 of the refill container 20 and the retention ring 420 is adjacent to the front section 30 of the refill container 20. Specifically, the compliance module 12D is attached to the refill container 20, whereby a curved gripping section 440 provided by the clip 40 compressively grips the rear section 32 of the refill container 20, while a retention aperture 450 provided by the retention ring 420 receives the dome pump 80 therethrough. To ensure that the compliance module 12D remains in place when attached to the refill container 20, the coupling arches 430 impart a compression force to both the retention arm 410 and the retention ring 420.

Embedded within the retention arm 410 is the communication module 240 previously discussed with regard to compliance module 12B. As such, the control actuator 246 is positioned so as to be substantially aligned with the dome pump 80 when the compliance module 12D is attached to the refill container 20.

Thus, during operation of the compliance module 12D, the dome pump 80 and the control actuator 246 are engaged by the user's hands or fingers to dispense material from the refill container 20. Simultaneously, the communication module 240 wirelessly transmits the hygiene compliance signal, compliance data, and associated unique identification code to the remote monitoring station 14, which records the received compliance signal as a completed hygiene event associated with the unique compliance module identification code.

Figure 10A:
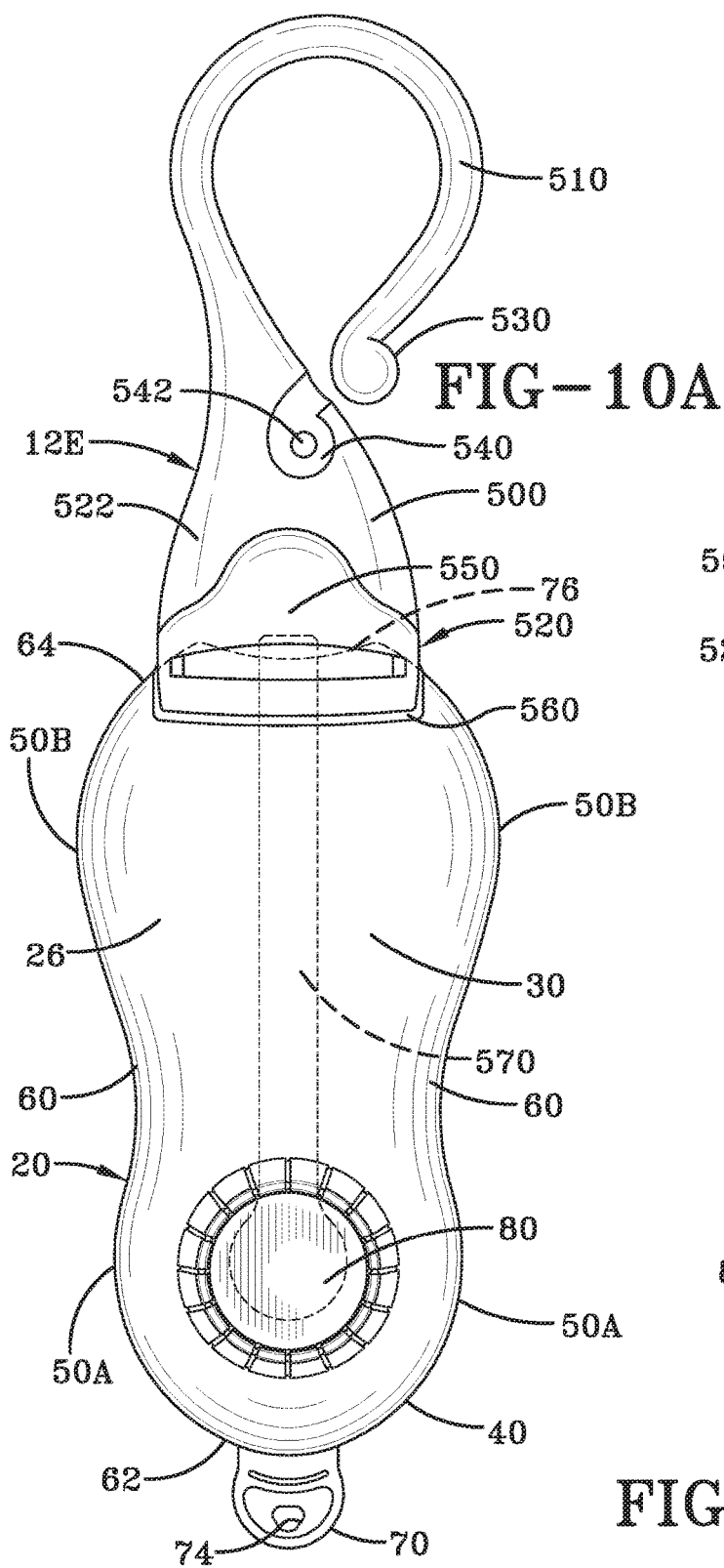
FIG. 10A is an elevational view of an alternate portable compliance dispenser having a compliance module that is attached to the refill container by a clip in accordance with the concepts of the present invention.
Figure 10B:
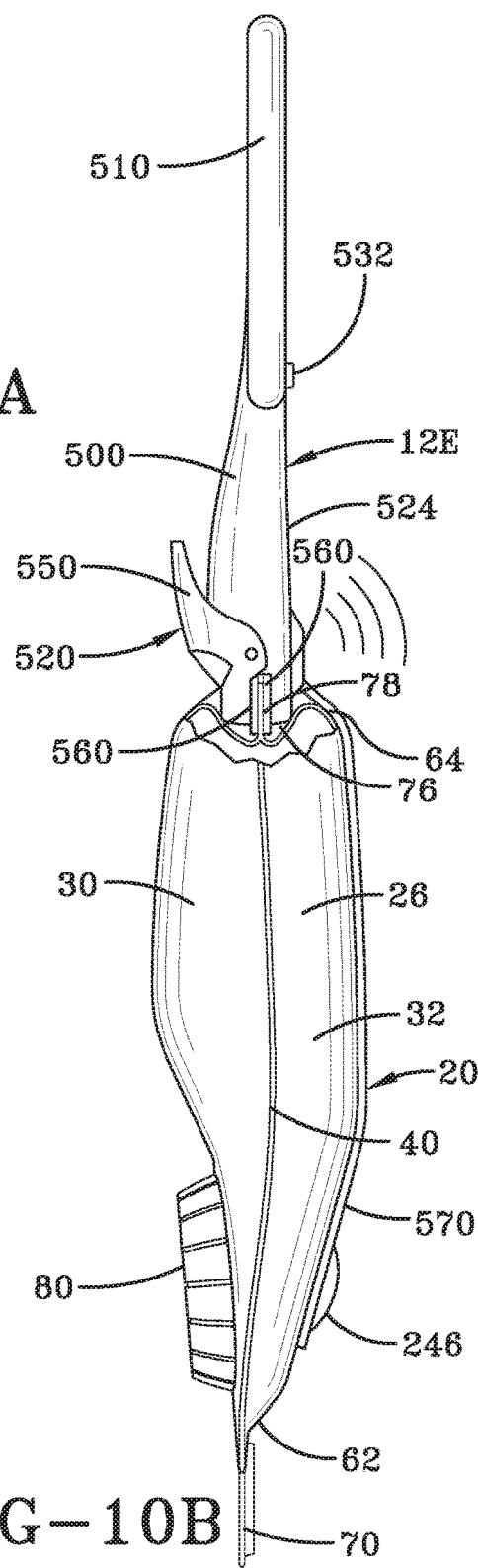
FIG. 10B is a side elevational view showing the portable compliance dispenser of FIG. 10A in accordance with the concepts of the present invention.
Figure 10C:
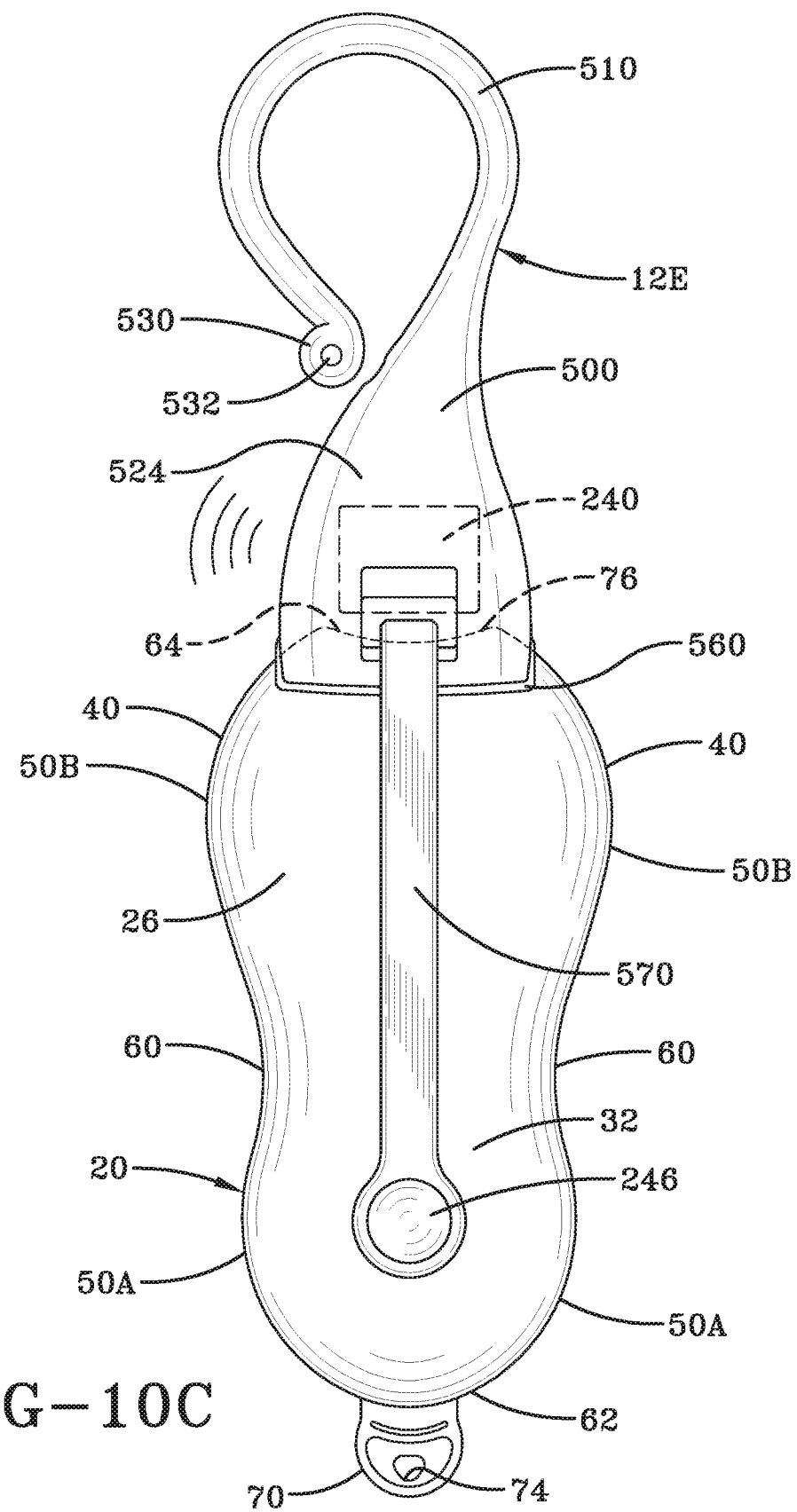
FIG. 10C is a rear elevational view of the portable compliance dispenser of FIG. 10A in accordance with the concepts of the present invention.

In yet another embodiment of the portable compliance dispenser 10, a portable compliance module 12E for use with the refill container 20 is shown in FIGS. 10A-C. The compliance module 12E comprises a substantially elongated body 500 that has a hook 510 at one end and an attachment clamp 520 at its other end. The body 500 has opposed front and rear surfaces 522,524, and may be formed from any suitable material, such as plastic, aluminum, or the like. The hook 510 is dimensioned to attach to any suitable structure, such as a belt loop of a user, for example. The end of the hook 510 also includes a curved end 530 from which extends a lock tab 532. The curved end 530 of the hook 510 is dimensioned to be received and retained within a correspondingly shaped depression 540 disposed in the body 500. To prevent the curved end 530 from inadvertently becoming disengaged from the body 500, the depression 540 includes a lock aperture 542 that is dimensioned to receive the lock tab 532. Thus, when the curved end 530 of the hook 510 is inserted into the depression 540, a closed loop is formed, which secures the compliance module to the user wearing the compliance module 12E.

The attachment clamp 520 includes lock arm 550 that when actuated, opens and closes a pair of substantially parallel and opposed jaws 560 that are configured to compressively engage the attachment section 78, as shown in FIG. 2C, of the refill container 20 that is disposed in the cavity 76. As such, the attachment clamp 520 allows the communication module 12E to be readily removed and attached to the refill container 20 as needed.

Extending from the rear surface 524 of the body 500 is an extension section 570, shown in FIG. 10C, which may be formed of any suitable material such as plastic or metal, which follows the contour of the rear section 32 of the refill container 20. The extension section 570 carries the control actuator 246 that is coupled to the communication module 240 that is disposed within the body 500. Specifically, the control actuator 246 is mounted at a position that is substantially aligned with the dome pump 80 of the attached refill container 20. Thus, when the control actuator 246 and dome pump 80 are engaged, the refill container 20 dispenses the liquid material while the compliance module 12E simultaneously transmits the hygiene compliance signal and data, along with the compliance module identification code, to the monitoring station 14 as previously discussed.

Figure 11A:
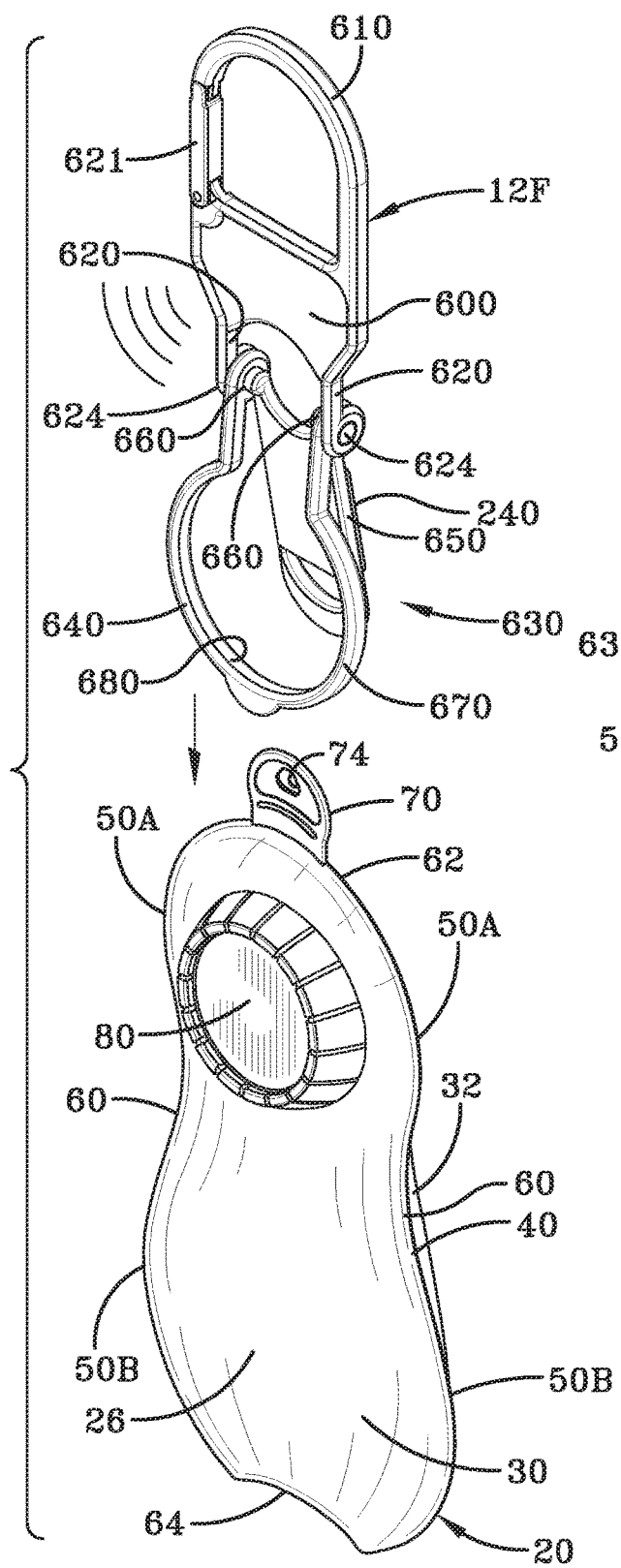
FIG. 11A is a perspective view of an alternate portable compliance dispenser that includes a compliance module that includes a carabiner clip and separated from the refill container in accordance with the concepts of the present invention.
Figure 11B:
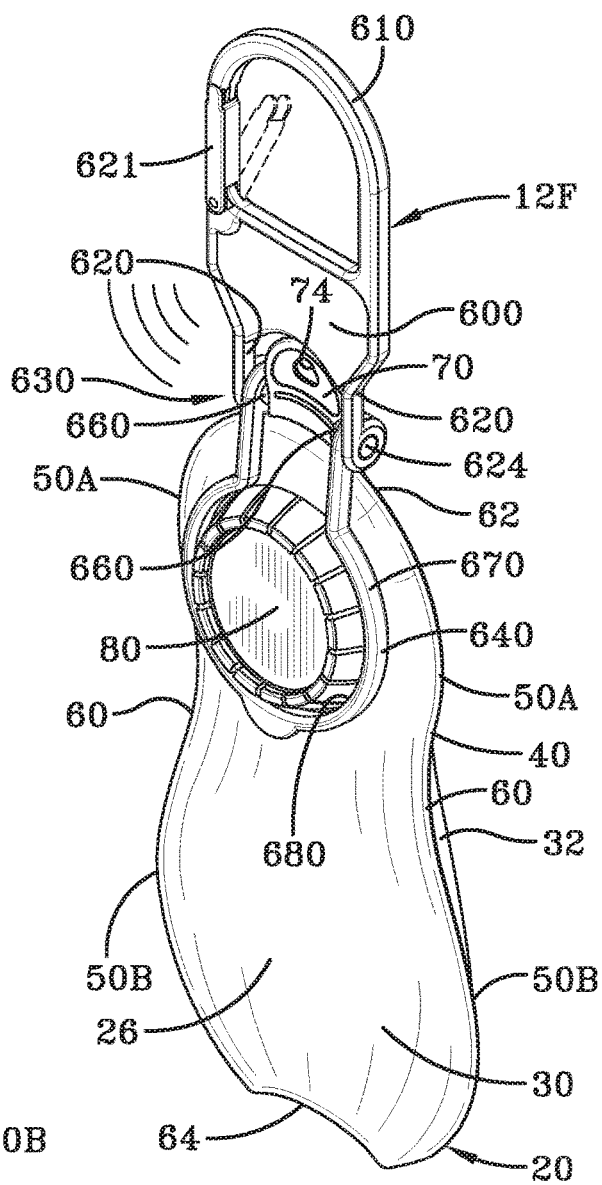
FIG. 11B is a perspective view of the portable compliance dispenser of FIG. 11A attached to the refill container in accordance with the concepts of the present invention.
Figure 11C:
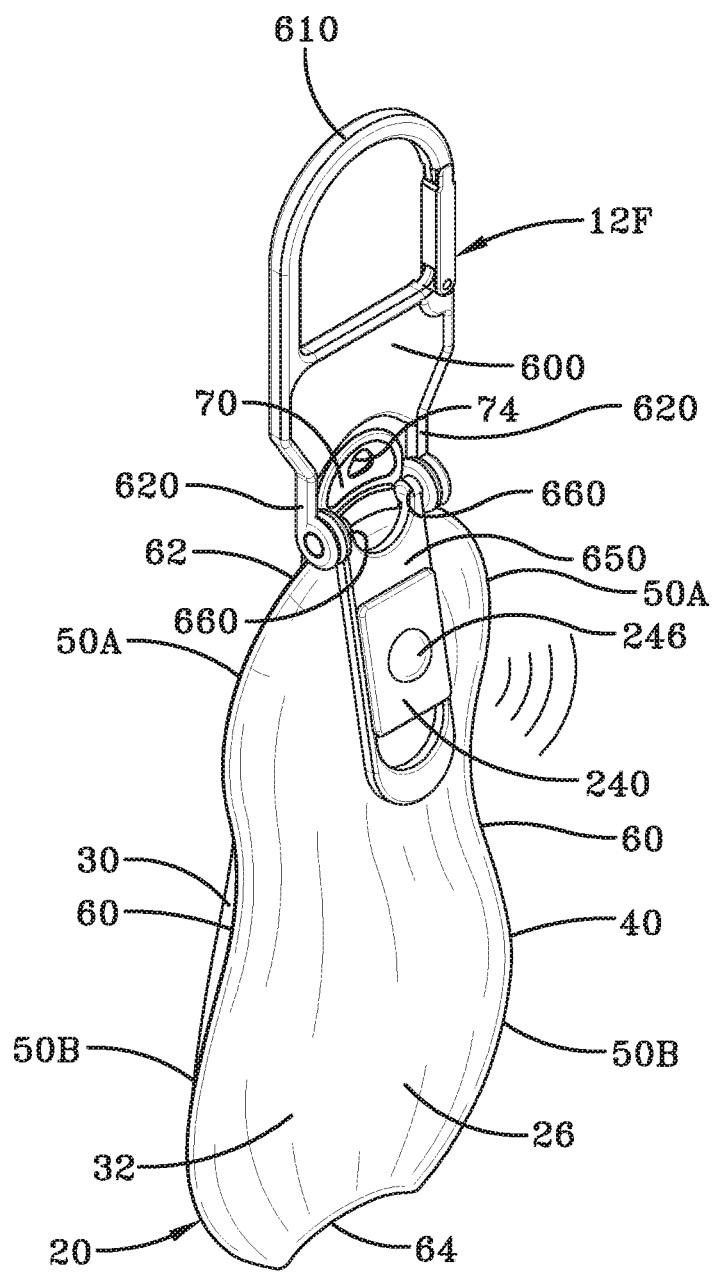
FIG. 11C is a rear perspective view of the portable compliance dispenser of FIG. 11A in accordance with the concepts of the present invention.

In yet another embodiment of the portable compliance dispenser 10, a compliance module 12F for use with the refill container 20 is shown in FIGS. 11A-C. Specifically, the communication module 12F comprises a body 600 from which extends an attachment clip 610, such as a carabiner clip, at one end and a pair of pivot arms 620 at another end. The attachment clip 610 includes a spring-biased closure arm 621, allowing the compliance module 12F to be removably attached to any desired item or structure provided by a user. Pivotably attached to the pivot arms 620 at a pivot point 624 is a mounting clip 630. The mounting clip 630 comprises a lock arm 640 and control arm 650 that extend from each other at an angle at attachment points 660. That is, the lock arm 640 and the control arm 650 comprising the mounting clip 630 are rigidly attached to each other at attachment points 660, while the mounting clip 630 is pivotably attached to the pivot arms 620 that extend from the body 600 at the pivot points 624. In addition, the lock arm 640 includes a retainer 670 that includes a retaining aperture 680 that is dimensioned to receive the dome pump 80 provided by the refill container 20 therethrough.

The compliance module 12F is attached to the refill container 20, such that the lock arm 640 and the control arm 650 are configured to slide over the dispensing end 62 of the refill container 20. During the attachment of the control module 12F to the refill container, the retainer 670 of the lock arm 640 is slid over the dome pump 80, so that it is received within the retaining aperture 680, while the control arm 650 applies a compressive force to the rear section 32 of the refill container 20. It should be appreciated that the dome pump 80 of the refill container 20 may be snap-fit into the retaining aperture 680 of the retainer 670, so as to attach the compliance module 12F to the refill container 20 without the compressive action of the control arm 650. Once the dome pump 80 is received within the retainer 670, the compressive force generated between the lock arm 640 and the control arm 650 is imparted to the refill container 20, thus retaining the compliance module 12F to the refill container 20.

Disposed within the control arm 650 of the compliance module 12F is the communication module 240, as previously discussed. The communication module 240 is configured such that the control actuator 246 is substantially aligned with the dome pump 80 when the compliance module 12F is attached to the refill container 20. This ensures that the control actuator 246 is engaged to denote a completed hygiene event when the dome pump 80 is depressed to dispense liquid material from the refill container 20. Alternatively, the compliance module 12F may be configured, such the pivoting motion of the control arm 650 allows the control actuator 246 to be moved so that it is compressed by the body 600 of the compliance module 12F, thus indicating a completed hygiene event.

Thus, during operation of the compliance module 12F, when the control actuator 246 and the dome pump 80 are depressed, liquid material is dispensed from the refill container 20, and a wireless hygiene compliance signal and data, along with the unique compliance module identification code, are wirelessly transmitted to the remote monitoring system 14, as previously discussed.

Figure 12:
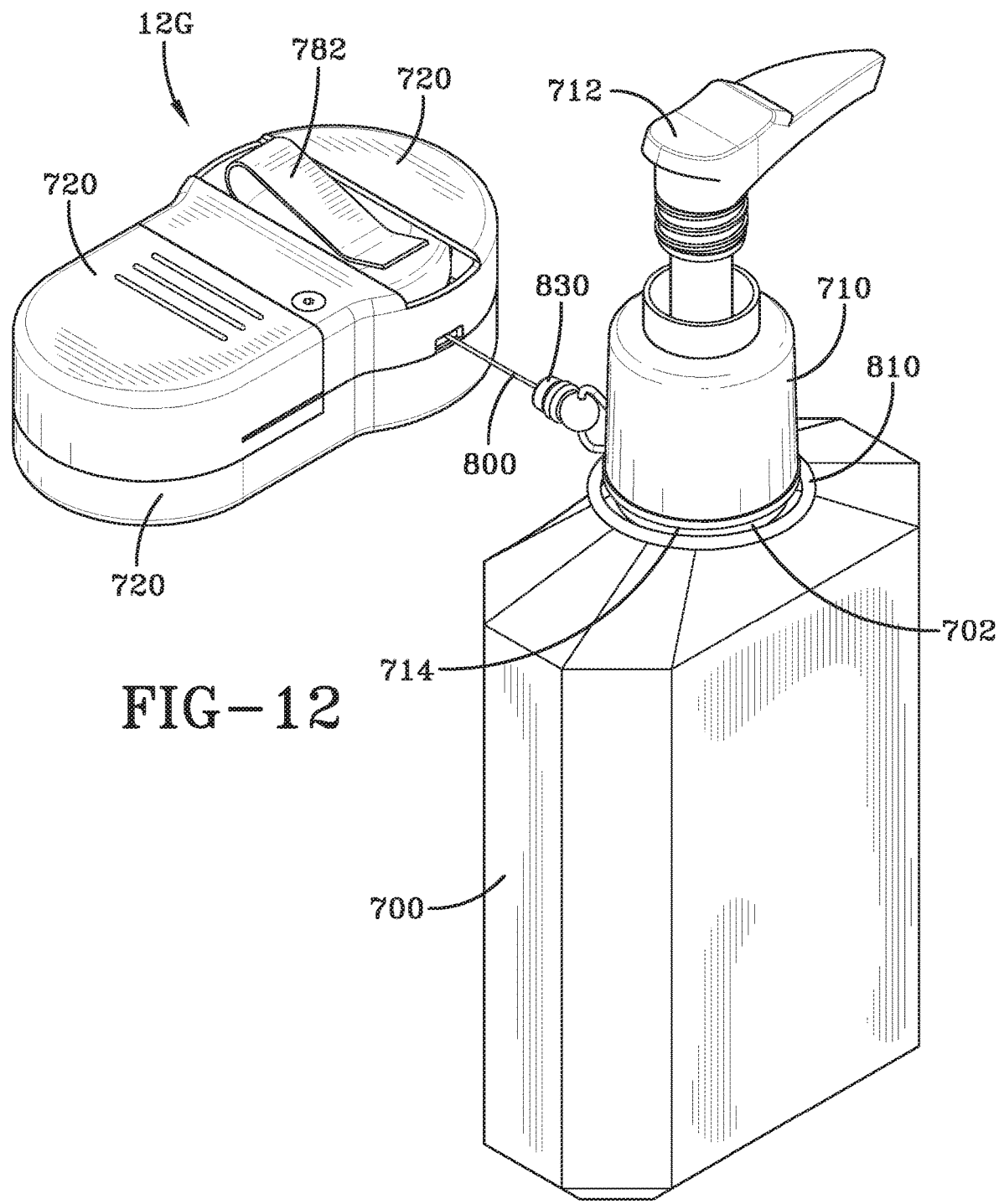
FIG. 12 is a perspective view of another embodiment of a portable compliance dispenser in accordance with the concepts of the present invention.
Figure 13:
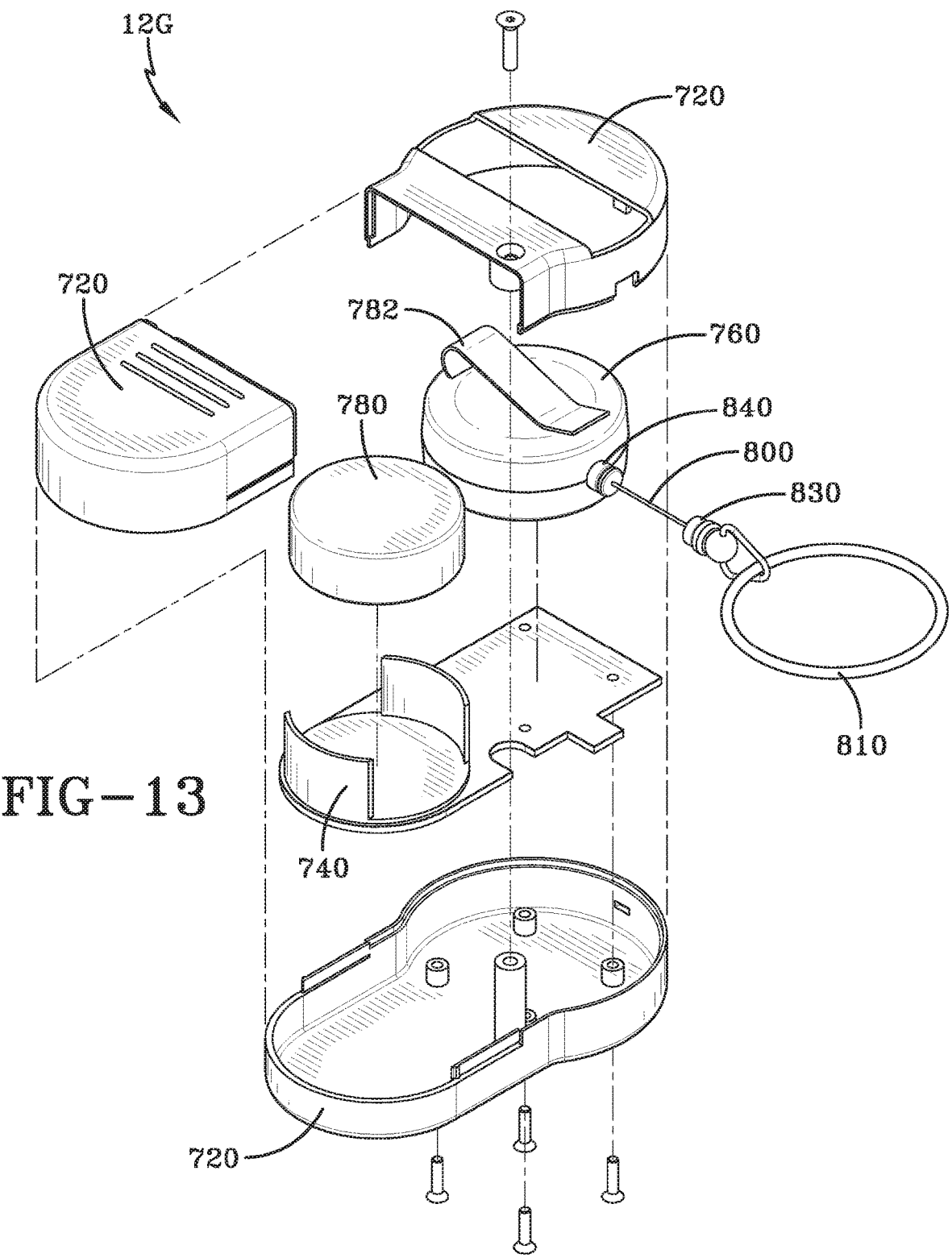
FIG. 13 is an exploded view of the portable compliance dispenser of FIG. 12 in accordance with the concepts of the present invention.
Figure 14:
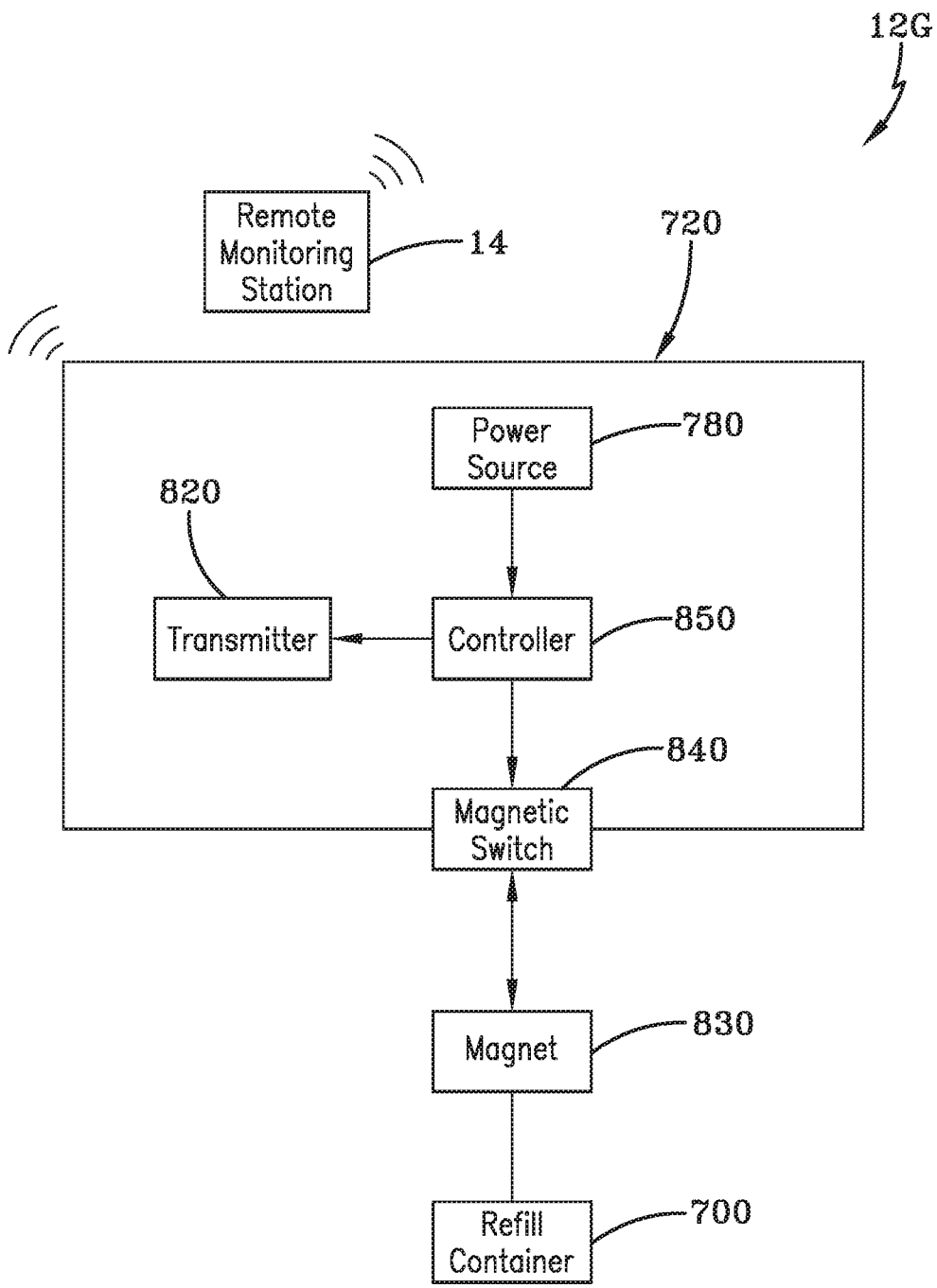
FIG. 14 is a block diagram of the portable compliance dispenser of FIG. 12 in accordance with the concepts of the present invention.

In another embodiment of the portable compliance dispenser 10, a portable compliance module 12G for use with the refill container 20 is shown in FIGS. 12-15. Specifically, the compliance module 12G is configured to be used with a dispensing container 700 having a neck 702 to which an annular collar 710 is threadably attached, as shown in FIG. 12, or other attachment point, such as an attachment aperture for example. The dispensing container 700 includes a pump 712 extending through the collar 710 that when actuated dispenses any suitable liquid material, such as soap or sanitizer for example, therefrom. Specifically, the collar 710 provides an annular collar edge 714 that circumscribes the neck 702 of the dispensing container 700.

The compliance module 12G includes a housing 720 that carries a support member 740 to which a tether retractor 760 and a power source 780, such as a battery, are attached. The housing also includes a carrying clip 782 that is configured to be attached to an individual's belt or other item to allow the compliance module 12G to be worn. The tether retractor 760 is configured to retract a tether 800 that is coupled at one end to the tether retractor 760 and that is coupled at its other end to a retainer 810. The tether 800 may comprise any suitable material as discussed above with regard to tether 114, while the retainer 810 is dimensioned to have a substantially annular shape to allow it to be stretched around the collar 710 so that is retained under its collar edge 714 to thus couple the compliance module 12G to the dispensing container 700. That is, the retainer 810 is made from any suitable stretchable material, such as rubber for example, that allows the retainer 810 to be stretched around the collar 710, whereupon it compresses or constricts about the neck 702 of the dispensing container 700, such that it engages the collar edge 714 of the collar 710. In another aspect, the retainer 810 may comprise a clip or hook that is configured to be attached to the attachment aperture (not shown) provided by the dispensing container 700. It should be appreciated that the tether 800 comprises a retractable cable that is spring biased, or an elastic cord that urges the magnet 830 and the magnetic switch 840 together. The retainer 810 also includes A container magnet 830 attached thereto, the presence of which is detected by a magnetic switch 840 that is carried by the tether retractor 760 to be discussed. In addition, the tether retractor 760 includes a controller 850 that is coupled to the magnetic switch 840, the power source 780, and to a transmitter 870.

Figure 15B:
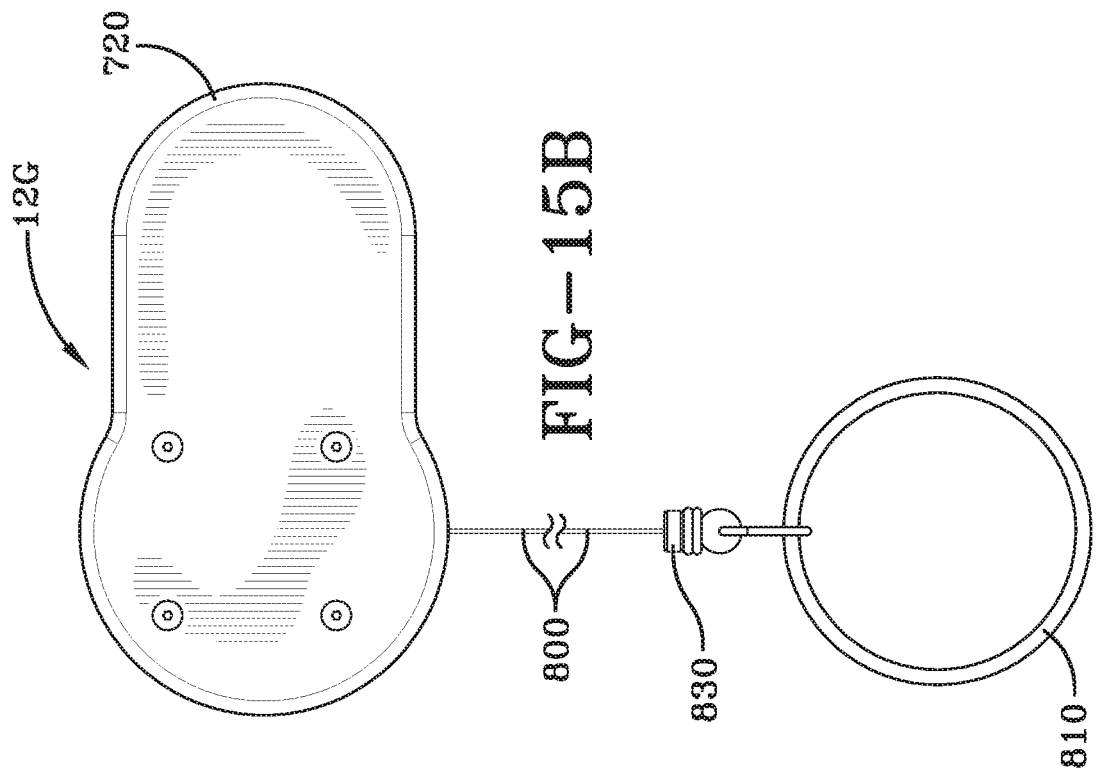
FIG. 15B is an elevational view of the portable compliance dispenser of FIG. 12 showing a tether in an extended position in accordance with the concepts of the present invention.
Figure 15A:
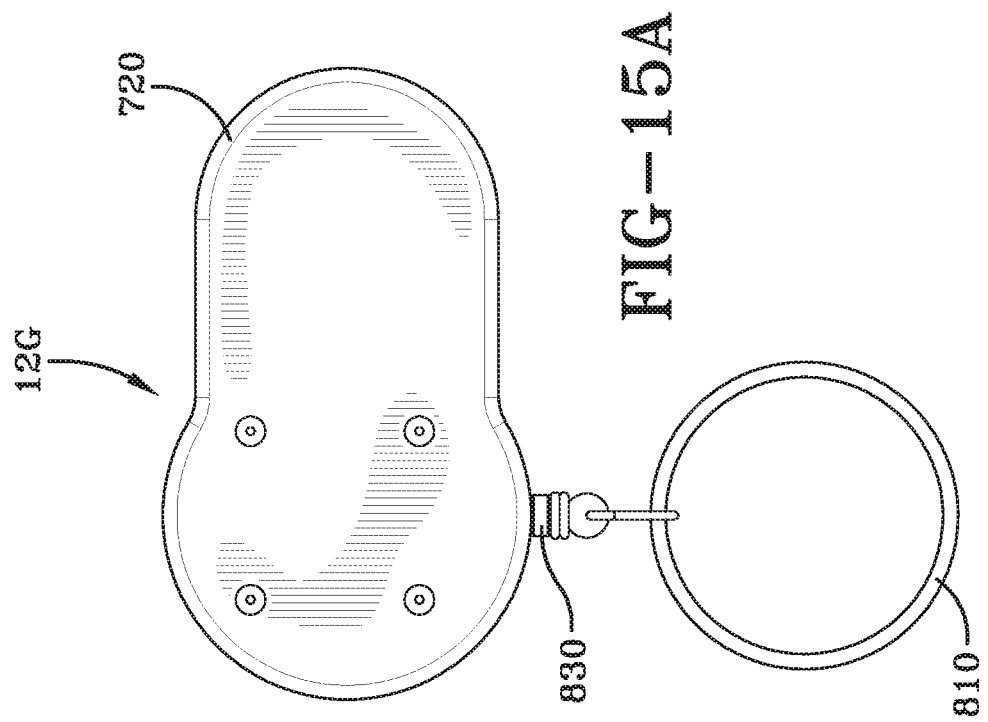
FIG. 15A is an elevational view of the portable compliance dispenser of FIG. 12 showing the tether in a retracted position in accordance with the concepts of the present invention.

Thus, during operation of the compliance module 12G, the dispensing container 700 is fully retracted by the tether 800 so that the presence of the container magnet 830 is magnetically detected by the magnetic switch 840, as shown in FIG. 15A. However, when the user desires to dispense material from the container 700 the container magnet 830 is moved away from the magnetic switch 840, as shown in FIG. 15B. As the magnetic switch 840 detects the removal of the container magnet 830 out of its detection range, the transmitter 870 transmits a wireless hygiene compliance signal or compliance data to the remote monitoring station 14 to indicate that material is being dispensed from the dispensing container 700, and that a hygiene compliance event has occurred. Moreover, when the magnetic switch 840 detects the presence or proximity of the container magnet 830, the controller 850 acknowledges that the dispensing container 700 is not being used to dispense material therefrom and the transmission of the compliance signal or data by the transmitter 870 is terminated.

It will, therefore, be appreciated that one advantage of one or more embodiments of the present invention is that a portable compliance dispenser can be removably coupled to a refill container that contains any liquid material, such as soap, sanitizer, or moisturizer. Another advantage of the present invention is that the portable compliance dispenser is configured to wirelessly transmit hygiene compliance data to monitor the usage of the refill container each time the dispenser is actuated. Still another advantage of the present invention is that the portable compliance dispenser can be easily worn or carried by a user.

Although the present invention has been described in considerable detail with reference to certain embodiments, other embodiments are possible. Therefore, the spirit and scope of the appended claims should not be limited to the description of the embodiments contained herein.

What is claimed is:

1. A portable dispenser worn by an individual comprising:
a refill container defining an interior within which a material is contained and from which the material is dispensed; and
a compliance module attached to the refill container, the compliance module comprising:
an attachment clip comprising a container magnet attached to the refill container;
a magnetic switch to detect a proximity of the container magnet;
a tether attached to the attachment clip; and
a carrying case attached to the tether, the carrying case urging the tether into a retracted position in which the carrying case is adjacent to the refill container, the carrying case housing a communication module within an interior of the carrying case,
wherein: the refill container and the magnetic switch are separated by a first distance when the tether is in the retracted position and the magnetic switch detects the container magnet being within a detection range of the magnetic switch,
the refill container and the magnetic switch are separated by a second distance when the tether is in an extended position and the magnetic switch detects the container magnet being out of the detection range of the magnetic switch, the second distance greater than the first distance,
the communication module detects a dispense event based on the detection of the proximity of the container magnet when the refill container moves from the first distance from the magnetic switch to the second distance from the magnetic switch, and
the communication module transmits a wireless hygiene compliance data of the individual to a remote monitoring station based on the dispense event via a transmitter coupled to a controller of the communication module and disables the transmitter when the tether is retracted from the second distance to the first distance.

2. The portable dispenser of claim 1, wherein the carrying case comprising a carrying clip.

3. The portable dispenser of claim 1, the carrying case comprising a base and a lid that define the interior of the carrying case.

4. The portable dispenser of claim 1, wherein: the refill container extends between an attachment end and a dispensing end, and the material is dispensed through a dispensing port at the dispensing end of the refill container.

5. A portable dispenser worn by an individual comprising:
a refill container defining an interior within which a material is contained and from Which the material is dispensed; and
a compliance module attached to the refill container, the compliance module comprising:
an attachment clip comprising a container magnet attached to the refill container;
a magnetic switch to detect a proximity of the container magnet; and
a tether having a first end, which is attached to the attachment clip, and a second end, which is attached to the magnetic switch, the tether movable between a retracted position, in which the magnetic switch is in a first state, when the magnetic switch detects the container magnet being within a detection range of the magnetic switch, and an extended position, in which the magnetic switch is in a second state when the magnetic switch detects the container magnet being out of the detection range of, the magnetic switch, wherein:

a transmitter coupled to a controller of the compliance module is enabled to transmit a compliance signal of the individual to a remote monitoring station indicative of a dispense event when the magnetic switch is in the second state, and the transmitter is not enabled to transmit the compliance signal when the magnetic switch is in the first state.

6. The portable dispenser of claim 5, wherein the refill container extends between an attachment end and a dispensing end wherein the material is dispensed through a dispensing port at the dispensing end of the refill container.

7. The portable dispenser of claim 6, wherein the refill container comprises a dome pump proximal the dispensing end and the material is dispensed through the dispensing port when the dome pump is depressed.

8. The portable dispenser of claim 6, wherein the refill container has a curved sidewall between the attachment end and the dispensing end such that the refill container has a first width at a first location between the attachment end and the dispensing end, a second width at a second location between the attachment end and the dispensing end, and a third width at a third location between the attachment end and the dispensing end.

9. The portable dispenser of claim 8, wherein the second location is between the first location and the third location and the second width is less than the first width and less than the third width.

10. The portable dispenser of claim 5, wherein the refill container comprising: a wall that defines the interior, wherein a pump of the portable dispenser is attached to the wall.

11. The portable dispenser of claim 10, wherein an actuation of the pump is configured to dispense the material from the refill container.

12. The portable dispenser of claim 5, the compliance module comprising a carrying case attached to the second end of the tether, the magnetic switch attached to the second end of the tether via the carrying case, the carrying case urging the tether into the retracted position in which the carrying case is adjacent to the refill container.

13. The portable dispenser of claim 12, the carrying case comprising a carrying clip.

14. A portable dispenser worn by an individual comprising:

a refill container defining an interior within which a material is contained and from which the material is dispensed; and a compliance module attached to the refill container, the compliance module comprising:

an attachment clip attached to the refill container;

a magnet attached to the attachment clip;

a magnetic switch to detect a proximity of the magnet; and a tether having a first end, which is attached to the magnet, and a second end which is attached to the magnetic switch, the tether movable between a retracted position, in which the magnetic switch is in a first state and detects a presence of the magnet being within a detection range of the magnetic switch, and an extended position, in which the magnetic switch transitions to a second state caused by movement of the tether and does not detect the presence of the magnet, when the tether is in the extended position the refill container is outside of the detection range of the magnetic switch, wherein:

a transmitter coupled to a controller of the compliance module is enabled to transmit a compliance signal of the individual to a remote monitoring station indicative of a dispense event when the magnetic switch is in the second state, and the transmitter is not enabled to transmit the compliance signal when the magnetic switch is in the first state.

15. The portable dispenser of claim 14, wherein the refill container extends between an attachment end and a dispensing end, wherein the material is dispensed through a dispensing port at the dispensing end.

16. The portable dispenser of claim 15, wherein the refill container has a curved sidewall between the attachment end and the dispensing end such that the refill container has a first width at a first location between the attachment end and the dispensing end, a second width at a second location between the attachment end and the dispensing end, and a third width at a third location between the attachment end and the dispensing end, and wherein the second location is between the first location and the third location and the second width is less than the first width and less than the third width.

17. The portable dispenser of claim 14, the refill container comprising:

a wall that defines the interior, wherein a pump of the portable dispenser is attached to the wall.

18. The portable dispenser of claim 17, wherein an actuation of the pump is configured to dispense the material from the refill container.

19. The portable dispenser of claim 14, the compliance module comprising a carrying case attached to the second end of the tether, the magnetic switch attached to the second end of the tether via the carrying case, the carrying case urging the tether into the retracted position in which the carrying case is adjacent to the refill container.

20. The portable dispenser of claim 19, the carrying case comprising a carrying clip.

* * * * *